United States Patent
Kopach et al.

(10) Patent No.: US 12,304,938 B2
(45) Date of Patent: May 20, 2025

(54) PROCESSES AND INTERMEDIATES FOR PREPARING TIRZEPATIDE

(71) Applicant: Eli Lilly and Company, Indianapolis, IN (US)

(72) Inventors: Michael Eugene Kopach, Greenwood, IN (US); Rachel Nicole Richey, Indianapolis, IN (US); Mark Richard Berglund, Zionsville, IN (US); Kevin Dale Seibert, Carmel, IN (US); Emily Suzanne Murzinski, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 18/806,394

(22) Filed: Aug. 15, 2024

(65) Prior Publication Data
US 2024/0400636 A1    Dec. 5, 2024

Related U.S. Application Data

(63) Continuation of application No. PCT/US2023/086530, filed on Dec. 29, 2023.

(60) Provisional application No. 63/477,734, filed on Dec. 29, 2022.

(51) Int. Cl.
*C07K 14/605*  (2006.01)
*C07K 14/00*   (2006.01)

(52) U.S. Cl.
CPC .......... *C07K 14/605* (2013.01); *C07K 14/001* (2013.01)

(58) Field of Classification Search
CPC .............................. C07K 14/605; C07K 14/001
See application file for complete search history.

(56) References Cited

U.S. PATENT DOCUMENTS

2022/0135639 A1    5/2022    Coffin et al.

FOREIGN PATENT DOCUMENTS

| WO | 2010029159 | 3/2010 |
| WO | 2010125079 | 11/2010 |
| WO | 2016111971 | 7/2016 |
| WO | 2020/159949 A1 | 8/2020 |

OTHER PUBLICATIONS

Chavda, Vivek P., et al. "Tirzepatide, a new era of dual-targeted treatment for diabetes and obesity: a mini-review." Molecules 27.13 (2022): 4315.
Frederick, Michael O., et al. "Kilogram-scale GMP manufacture of tirzepatide using a hybrid SPPS/LPPS approach with continuous manufacturing." Organic Process Research & Development 25.7 (2021): 1628-1636.
Han, So-Yeop, and Young-Ah Kim. "Recent development of peptide coupling reagents in organic synthesis." Tetrahedron 60.11 (2004): 2447-2467.
International Search Report and Written Opinion in International Application No. PCT/US2023/086530, dated Sep. 5, 2024, 23 pages.
Mroz, Piotr A., et al. "Optimized GIP analogs promote body weight lowering in mice through GIPR agonism not antagonism." Molecular Metabolism 20 (2019): 51-62.
Nyfeler, Rolf. "Peptide synthesis via fragment condensation." Peptide Synthesis Protocols (1995): 303-316.

*Primary Examiner* — Amber D Steele
(74) *Attorney, Agent, or Firm* — Parker D. McCrary; Michael R. Asam

(57) ABSTRACT

The present invention provides new intermediates and processes useful in the manufacture of tirzepatide, or a pharmaceutically acceptable salt thereof.

5 Claims, 7 Drawing Sheets

Specification includes a Sequence Listing.

PROCESSES AND INTERMEDIATES FOR PREPARING TIRZEPATIDE

RELATED APPLICATIONS

This application claims priority to U.S. Provisional Patent Application No. 63/477,734, filed Dec. 29, 2022, the entire content of which is incorporated herein by reference.

SEQUENCE LISTING

This application contains a Sequence Listing which has been submitted electronically in XML format and is hereby incorporated by reference in its entirety. The XML copy, created on Dec. 27, 2023, is named 02021-0166-00304_SL.XML and is 78,828 bytes in size.

DISCLOSURE

The present disclosure provides processes and intermediates for making a GIP/GLP1 dual agonist peptide, referred to herein as "tirzepatide," or a pharmaceutically acceptable salt thereof.

Diabetes mellitus is a chronic disorder characterized by hyperglycemia resulting from defects in insulin secretion, insulin action, or both. In type 2 diabetes mellitus ("T2D"), the combined effects of impaired insulin secretion and insulin resistance are associated with elevated blood glucose levels. The GIP/GLP1 dual agonist, tirzepatide ("TZP"), is described and claimed in U.S. Pat. No. 9,474,780. Tirzepatide can be useful in the treatment of T2D. U.S. Pat. No. 9,474,780 is incorporated by reference herein in its entirety.

The preparation of large-scale, pharmaceutically-acceptable tirzepatide presents a number of technical challenges that may affect the overall yield and purity. There is a need for processes and intermediates to enable improved or alternative methods for production of tirzepatide. Similarly, there is a need for efficient and environmentally "green" processes, including stable intermediates, to produce tirzepatide with fewer purification steps. Improved, or alternative technology is also needed to provide tirzepatide manufacturing processes that produce minimal waste streams for both environmental and operator enhanced safety. There is also a need for processes to avoid the use of transition metals and/or harsh reaction conditions that are incompatible with peptide synthesis.

The present disclosure seeks to meet these needs by providing novel intermediates and processes useful in the manufacture of tirzepatide (SEQ ID NO: 1), or a pharmaceutically acceptable salt thereof. The tirzepatide manufacturing processes of the present disclosure provide intermediates and process reactions embodying a combination of advances, including an efficient route having fewer steps, while at the same time maintaining high quality and purity. In addition, the new processes and intermediates decrease resource intensity and minimize waste streams.

The new processes described herein provide various embodiments of intermediates useful for production of tirzepetide.

SUMMARY

The present disclosure describes methods of preparing tirzepatide or a pharmaceutically acceptable salt thereof.

In certain embodiments, the present disclosure describes methods of preparing tirzepatide or a pharmaceutically acceptable salt thereof, the method comprising: (a) coupling a peptide of SEQ ID NO: 10 to SEQ ID NO: 11 to form a peptide of SEQ ID NO: 12; and (b) deprotecting the peptide of SEQ ID NO: 12 to obtain tirzepatide or a pharmaceutically acceptable salt thereof. In certain embodiments, the peptide of SEQ ID NO: 12 from step (a) is isolated prior to the deprotection step (b). In certain embodiments, the peptide of SEQ ID NO: 12 from step (a) is washed before the deprotection step (b). In certain embodiments, the peptide of SEQ ID NO: 12 from step (a) is washed after the deprotection step (b).

In certain embodiments, the present disclosure describes methods of preparing tirzepatide or a pharmaceutically acceptable salt thereof, the method comprising: (a) coupling a peptide of SEQ ID NO: 13 to SEQ ID NO: 14 to form a peptide of SEQ ID NO: 12; and (b) deprotecting the peptide of SEQ ID NO: 12 to obtain tirzepatide or a pharmaceutically acceptable salt thereof. In certain embodiments, the peptide of SEQ ID NO: 12 from step (a) is isolated prior to step (b). In certain embodiments, the peptide of SEQ ID NO: 12 from step (a) is washed before the deprotection step (b). In certain embodiments, the peptide of SEQ ID NO: 12 from step (a) is washed after the deprotection step (b).

In certain embodiments, the present disclosure describes methods of preparing tirzepatide or a pharmaceutically acceptable salt thereof, the method comprising: (a) coupling a peptide of SEQ ID NO: 15 to SEQ ID NO: 16 to form a peptide of SEQ ID NO: 12; and (b) deprotecting the peptide of SEQ ID NO: 12 to obtain tirzepatide or a pharmaceutically acceptable salt thereof. In certain embodiments, the peptide of SEQ ID NO: 12 from step (a) is isolated prior to step (b). In certain embodiments, the peptide of SEQ ID NO: 12 from step (a) is washed before the deprotection step (b). In certain embodiments, the peptide of SEQ ID NO: 12 from step (a) is washed after the deprotection step (b).

In certain embodiments, the present disclosure describes a compound of SEQ ID NO: 10, or a pharmaceutically acceptable salt thereof. In certain embodiments, the present disclosure describes a compound of SEQ ID NO: 10, or a pharmaceutically acceptable salt thereof, wherein the compound comprises one or more protecting groups. In certain embodiments, the one or more protecting groups are chosen from Fmoc, Boc, tert-butyl, and trityl groups. In certain embodiments, the compound does not comprise one or more of the protecting groups of SEQ ID NO: 10 (i.e., one or more protecting groups are removed from SEQ ID NO: 10). In certain embodiments, the compound does not comprise any of the protecting groups of SEQ ID NO: 10 (i.e., all the protecting groups are removed from SEQ ID NO: 10).

In certain embodiments, the present disclosure describes a compound of SEQ ID NO: 13, or a pharmaceutically acceptable salt thereof. In certain embodiments, the present disclosure describes a compound of SEQ ID NO: 13, or a pharmaceutically acceptable salt thereof, wherein the compound comprises one or more protecting groups. In certain embodiments, the one or more protecting groups are chosen from Fmoc, Boc, tert-butyl, and trityl groups.

In certain embodiments, the present disclosure describes a compound of SEQ ID NO: 14, or a pharmaceutically acceptable salt thereof. In certain embodiments, the present disclosure describes a compound of SEQ ID NO: 14, or a pharmaceutically acceptable salt thereof, wherein the compound comprises one or more protecting groups. In certain embodiments, the one or more protecting groups are chosen from Fmoc, Boc, tert-butyl, and trityl groups.

In certain embodiments, the present disclosure describes a compound of SEQ ID NO: 15, or a pharmaceutically acceptable salt thereof. In certain embodiments, the present disclosure describes a compound of SEQ ID NO: 15, or a pharmaceutically acceptable salt thereof, wherein the compound comprises one or more protecting groups. In certain embodiments, the one or more protecting groups are chosen from Fmoc, Boc, tert-butyl, and trityl groups. In certain embodiments, the compound does not comprise one or more of the protecting groups of SEQ ID NO: 15 (i.e., one or more protecting groups are removed from SEQ ID NO: 15). In certain embodiments, the compound does not comprise any of the protecting groups of SEQ ID NO: 15 (i.e., all the protecting groups are removed from SEQ ID NO: 15).

In certain embodiments, the present disclosure describes a compound of SEQ ID NO: 16, or a pharmaceutically acceptable salt thereof. In certain embodiments, the present disclosure describes a compound of SEQ ID NO: 16, or a pharmaceutically acceptable salt thereof, wherein the compound comprises one or more protecting groups. In certain embodiments, the one or more protecting groups are chosen from Fmoc, Boc, tert-butyl, and trityl groups. In certain embodiments, the compound does not comprise one or more of the protecting groups of SEQ ID NO: 16 (i.e., one or more protecting groups are removed from SEQ ID NO: 16). In certain embodiments, the compound does not comprise any of the protecting groups of SEQ ID NO: 16 (i.e., all the protecting groups are removed from SEQ ID NO: 16).

In certain embodiments, the present disclosure describes a process of preparing a compound of formula (I):

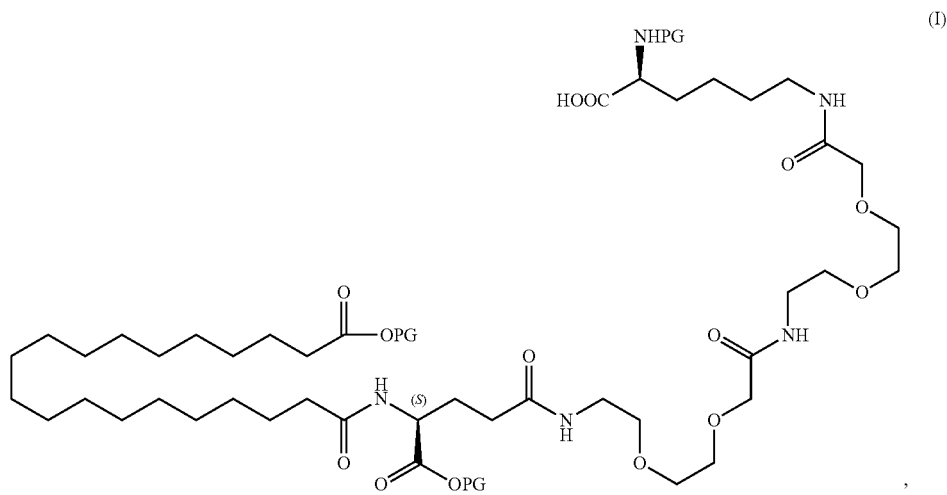

(I)

wherein PG is a protecting group, the process comprising:
(a) contacting a compound of formula (Ia) and diisopropylethylamine

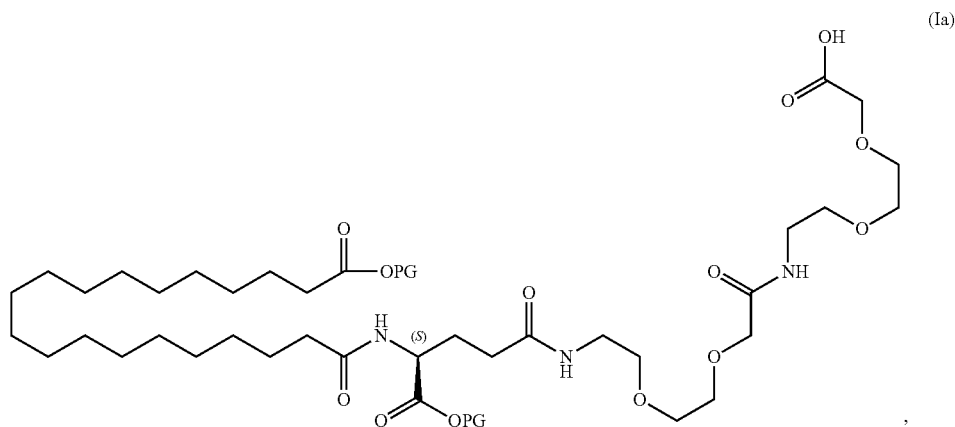

(Ia)

(b) contacting the product of step (a) with 2-(5-nor-bomene-2,3-dicarboximido)-1,1,3,3-tetramethyluronium tetrafluoroborates in DMF; and (c) adding a compound of formula (Ib) to the mixture of (b),

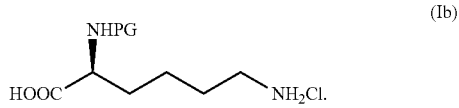
(Ib)

In certain embodiments, the protecting group is chosen from Boc and Fmoc. In certain embodiments, the protecting group is Fmoc. In certain embodiments, the process is conducted using continuous flow. In certain embodiments, the process is carried out in flow reactor.

In certain embodiments, the present disclosure describes a method that includes filtering tirzepatide or pharmaceutically acceptable salt thereof under one or more of the following conditions: (i) a temperature from 10 to 34° C., optionally about 20° C.; (ii) a turbulent flow/crossflow velocity from 1.94 to 2.46 m/s, optionally about 2.2 m/s; (iii) a laminar flow/shear rate from $2.1 \times 10^3$ to $2.7 \times 10^3$ 1/s, optionally about $2.4 \times 10^3$ 1/s; (iv) a primary product concentration from 32.8 to 47.2 mg/mL, optionally about 40 mg/mL; and (v) a secondary product concentration from 37 to 53 mg/mL, optionally about 45 mg/mL.

BRIEF DESCRIPTION OF THE DRAWINGS

FIG. 2A shows viscosity measurements for gelation studies related to process solvent. FIG. 2B shows viscosity measurements for gelation studies related to peptide concentration and gelation time. FIG. 2C and FIG. 2D show viscosity measurements for gelation studies related to peptide concentration and processing shear rate.

DETAILED DESCRIPTION

Figure 1A:
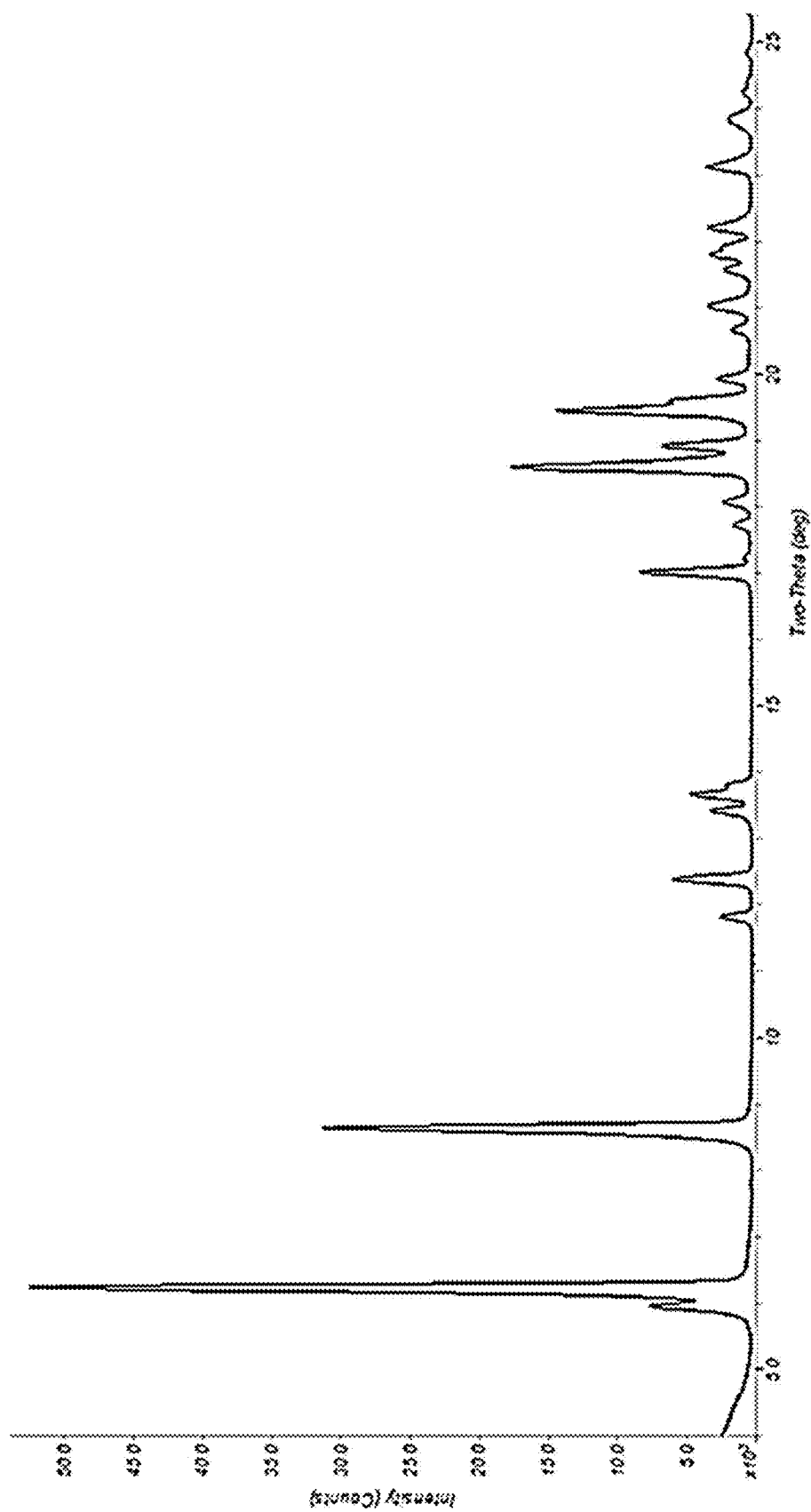
FIG. 1A, FIG. 1B, and FIG. 1C show representative XRPD patterns for Fmoc-G-P-S(tBu)-S(tBu)-G-OH (SEQ ID NO: 19) pentamer Form A, Form C, and Form D, respectively.
Figure 1B:
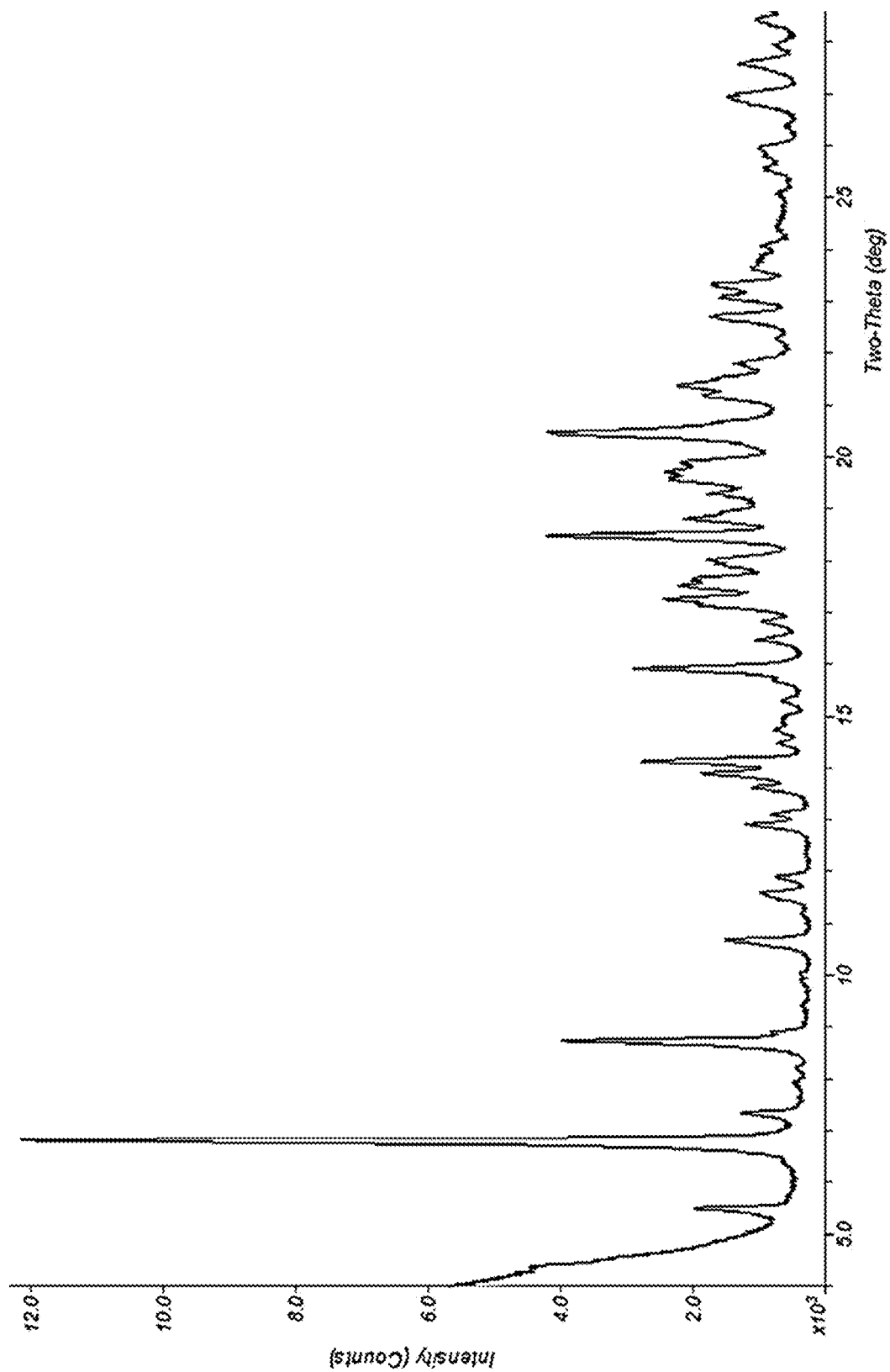

The present disclosure provides a method of preparing tirzepatide or a pharmaceutically acceptable salt thereof. In some embodiments, the method comprises a step (a) of coupling a peptide of SEQ ID NO: 10 to SEQ ID NO: 11 to form a peptide of SEQ ID NO: 12.

The present disclosure also provides a method of preparing tirzepatide or a pharmaceutically acceptable salt thereof, comprising a step (a) of coupling a peptide of SEQ ID NO: 13 to SEQ ID NO: 14 to form a peptide of SEQ ID NO: 12.

The present disclosure also provides a method of preparing tirzepatide or a pharmaceutically acceptable salt thereof, comprising a step (a) of coupling a peptide of SEQ ID NO: 15 to SEQ ID NO: 16 to form a peptide of SEQ ID NO: 12.

In some embodiments, the method further comprises a step (b) of deprotecting the peptide of SEQ ID NO: 12 to obtain tirzepatide or a pharmaceutically acceptable salt thereof.

In some embodiments, the method comprises isolating the coupled product of step (a) before carrying out the deprotection step (b). In some embodiments, the method comprises washing the coupled product of step (a) before the deprotection step (b). In some embodiments, the method comprises washing the coupled product of step (a) after the deprotection step (b).

Another aspect of the present disclosure provides for a compound of SEQ ID NO: 10, or a pharmaceutically acceptable salt thereof. In some embodiments the compound of SEQ ID NO: 10 comprises one or more protecting groups.

Another aspect of the present disclosure provides for a compound of SEQ ID NO: 13, or a pharmaceutically acceptable salt thereof. In some embodiments the compound of SEQ ID NO: 13 comprises one or more protecting groups.

Another aspect of the present disclosure provides for a compound of SEQ ID NO: 14, or a pharmaceutically acceptable salt thereof. In some embodiments the compound of SEQ ID NO: 14 comprises one or more protecting groups.

Another aspect of the present disclosure provides for a compound of SEQ ID NO: 15, or a pharmaceutically acceptable salt thereof. In some embodiments the compound of SEQ ID NO: 15 comprises one or more protecting groups.

Another aspect of the present disclosure provides for a compound of SEQ ID NO: 16, or a pharmaceutically acceptable salt thereof. In some embodiments the compound of SEQ ID NO: 16 comprises one or more protecting groups.

In some embodiments the one or more protecting groups are chosen from Fmoc, Boc, tert-butyl, and trityl groups, or combinations thereof. In some embodiments, the one or more protecting groups is Fmoc. In some embodiments, the one or more protecting groups is Boc. In some embodiments, the one or more protecting groups is tert-butyl. In some embodiments, the one or more protecting groups is trityl. In some embodiments, the compounds are protected with Fmoc, Boc, tert-butyl, and trityl groups. In some embodiments, the compounds are protected with Fmoc groups. In some embodiments, the compounds are protected with Fmoc and Boc groups. In some embodiments, the compounds are protected with Fmoc and tert-butyl groups. In some embodiments, the compounds are protected with Fmoc and trityl groups. In some embodiments, the compounds are protected with Boc groups. In some embodiments, the compounds are protected with Boc and tert-butyl groups. In some embodiments, the compounds are protected with Boc and trityl groups. In some embodiments, the compounds are protected with tert-butyl groups. In some embodiments, the compounds are protected with tert-butyl and trityl groups. In some embodiments, the compounds are protected with trityl groups. In some embodiments, the compounds are protected with Fmoc, Boc, and tert-butyl groups. In some embodiments, the compounds are protected with Fmoc, Boc, and trityl groups. In some embodiments, the compounds are protected with Boc, tert-butyl, and trityl groups. In some embodiments, the compounds are protected with Fmoc, tert-butyl, and trityl groups.

In some embodiments, one or more protecting groups are removed in step (b). In some embodiments, all the protecting groups are removed in step (b).

In another aspect of the present disclosure, there is provided a process of preparing a tirzepatide sidechain+lysine of formula (I):

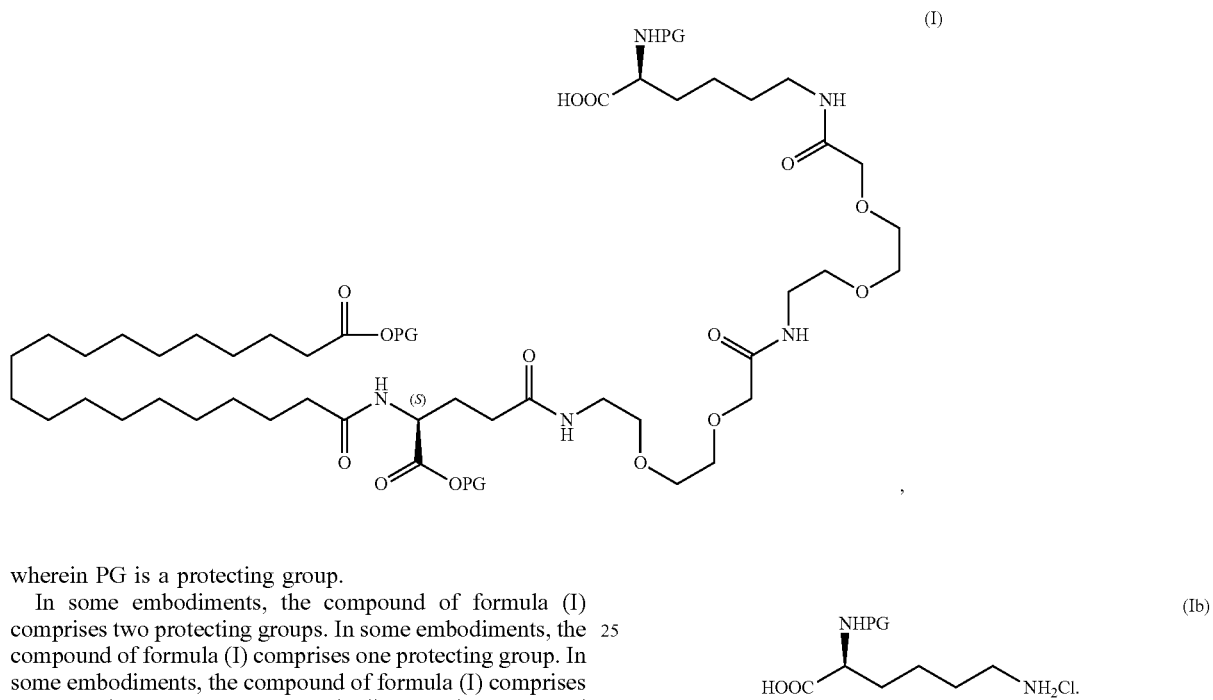

wherein PG is a protecting group.

In some embodiments, the compound of formula (I) comprises two protecting groups. In some embodiments, the compound of formula (I) comprises one protecting group. In some embodiments, the compound of formula (I) comprises no protecting groups. In some embodiments, the compound of formula (I) is used to make tirzepatide. In some embodiments, the compound of formula (I) is used to make tirzepatide using a linear SPPS method.

In some embodiments, the process of preparing a compound of formula (I) comprises a step (a) of contacting a compound of formula (Ia) and diisopropylethylamine:

In some embodiments, the protecting group of the compound of formula (I) is chosen from Boc and Fmoc. In some embodiments, the protecting group of the compound of formula (I) is Boc. In some embodiments, the protecting group of the compound of formula (I) is Fmoc.

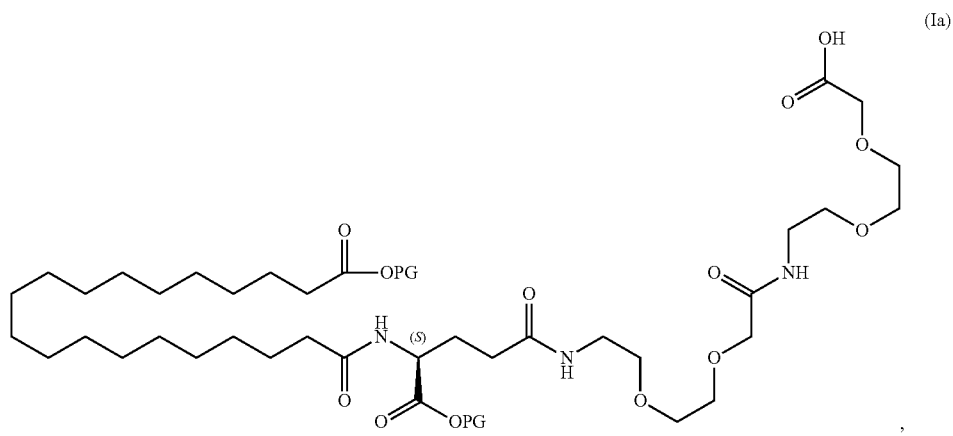

wherein PG is a protecting group.

In some embodiments, the process of producing a compound of formula (I) further comprises a step (b) of contacting the product of step (a) with 2-(5-norbornene-2,3-dicarboximido)-1,1,3,3-tetramethyluronium tetrafluoroborates in DMF. In some embodiments, the process comprises a step (c) of adding a protected lysine of formula (Ib) to the mixture of step (b):

In some embodiments, the process of producing a compound of formula (I) is conducted using continuous flow. In some embodiments, the process of producing a compound of formula (I) is carried out in flow reactor.

As used herein, the following abbreviations have the meanings as set forth herein: "AEEA" means 17-amino-10-oxo-3,6,12,15 tetraoxa-9-aza heptadecanoic acid; "API" means active pharmaceutical ingredient; "CTC" means chlorotrityl; "DIC" means diisopropylcarbodiimide; "DCC" means dicyclohexylcarbodiimide; "DCM" means dichloromethane; "DCU" means dicyclohexylurea; "DIEA" means N,N-diisopropylethylamine; "DMF" means dimethylformamide; "DTT" means dithiothreitol; "Fmoc" means fluorenylmethyloxycarbonyl chloride; "HATU" means (1-[bis(dimethylamino)methylene]-1H-1,2,3-triazolo[4,5-b]pyridinium 3-oxide hexafluorophosphate; "HFIP" means hexafluoroisopropanol; "IPA" means isopropanol; "L-GSH" means L-glutathione reduced solution; "LPPS" means liquid phase peptide synthesis; "MTBE" means methyl-tert-butyl ether; "OXYMA" means ethyl cyanohydroxyiminoacetate; "Pip" means piperidine; "SPPS" means Solid Phase Peptide Synthesis; "TFA" means trifluoroacetic acid; "TFET" means 2,2,2-trifluoroethanethiol; "TIPS" means triisopropylsilane; "TCEP" means tris(2-carboxyethyl)phosphine; "TMSA" means trimethylsilylacetamide; "TNTU" means 2-(5-Norbomene-2,3-dicarboximido)-1,1,3,3-tetramethyluronium tetrafluoroborate; "TZP" means tirzepatide; and "UPLC" means ultra-high performance liquid chromatography.

As presented herein, amino acid one letter abbreviations are presented in bold print, while atoms are presented as unbolded text, to distinguish from one letter amino acid abbreviations. As used herein, when an amino acid abbreviation appears with a number above the amino acid, the number refers to the corresponding amino acid position in the final tirzepatide product. The numbers are provided for convenience and the appearance or absence of such numbers in a sequence does not influence the amino acid sequence or the peptide indicated in such sequence.

As used herein, the term "protected" means that a protecting group is attached at the indicated position. The artisan will recognize that a variety of protecting groups are well known, and alternative protecting groups may be suitable for a particular process.

The term "protecting group" or "amino acid protecting group" as used herein refers to a group that protects an acid or amine moiety of the amino acid or a reactive moiety on the side chain of an amino acid. The "acid moiety" includes, for example, carboxylic acid group (—COOH). The "amine moiety" includes, for example, a primary amine group (—NH$_2$), a secondary amine group (—NH—), an amide group (—C(O)—NH$_2$), and a guanidinium group ([—NHC(NH$_2$)—NH$_2$]$^+$). The acid moiety or amine moiety may be a moiety of a terminal amino acid in a peptide or polypeptide or a moiety on a side chain of a non-terminal amino acid in a peptide or polypeptide. Other reactive moieties on the side chain of an amino acid include, for example, hydroxy (—OH) and thiol (—SH) groups.

A protecting group may be a removable group that is known in the art to (i) protect a reactive group (such an amine group or a carboxylic acid group) against undesirable reaction during synthetic procedures, e.g., to block or protect the functionality of the reactive group while the reactions involving other functional sites of the compound are carried out, and (ii) be selectively deprotected in a multiply-protected structure without affecting other protecting groups. Suitable protecting groups and the methods of introducing and removing such groups include those known in the art, such as those described in T. W. Green and P. G. M. Wuts, *Greene's Protective Groups in Organic Synthesis*, John Wiley and Sons, 2007 and Isidro-Llobet et al., *Amino Acid-Protecting Groups*, Chem. Rev, 2009, 109(6), 2455-2504, which are incorporated herein in their entirety.

Suitable protecting groups for aspartic acid (Asp) include, but are not limited to, tert-butyl (t-Bu), 3-methyl-3-pentyl (mpe), allyl, and 4-{N-[1-(4,4-dimethyl-2,6-dioxocyclohexylidene)-3-methylbutyl]amino}benzyl (DMAB). In some embodiments, the protecting group for aspartic acid (Asp) is t-Bu or mpe.

Suitable protecting groups for serine (Ser), threonine (Thr), or tyrosine (Tyr) include, but are not limited to, t-Bu and triphenylmethyl (trityl or trt). In some embodiments, the protecting group for serine (Ser), threonine (Thr), or tyrosine (Tyr) is t-Bu or TRT.

Suitable protecting groups for glutamic acid (Glu) include, but are not limited to, t-Bu, trt, allyl, and DMAB. In some embodiments, the protecting group for glutamic acid (Glu) is t-Bu or trt.

Suitable protecting groups for glutamine (Gln) include, but are not limited to, trt, 4-methoxytrityl (4-methyltrityl, or MTT), acetamidomethyl (ACM), and trimethoxybenzyl (TMOB). In some embodiments, the protecting group for glutamine (Gln) is TRT.

Suitable protecting groups for lysine (Lys) include, but are not limited to, t-butoxycarbonyl (Boc), allyloxycarbony (Alloc), 4-phenylacetoxybenzyloxycarbonyl (PhAc), MTT, 1-(4,4-dimethyl-2,6-dioxocyclohex-1-ylidene)ethyl (ivDde), and 2-(4,4-dimethyl-2,6-dioxocyclohexylidene)ethyl (Dde). In some embodiments, the protecting group for lysine (Lys) is Boc, MTT, or Alloc.

Suitable protecting groups for tryptophan (Trp) include, but are not limited to, Boc and formyl. In some embodiments, the protecting group for tryptophan (Trp) is Boc.

Suitable protecting groups for histidine (His) include, but are not limited to, Boc, trt, and 2,4-dinitrophenyl (dnp). In some embodiments, the protecting group for histidine (His) is Boc, trt, or dnp.

Exemplary acid protecting groups include esters such as substituted and unsubstituted $C_1$-$C_8$ lower alkyl (e.g., methyl, ethyl, t-butyl), methoxymethyl, methylthiomethyl, 2,2,2-trichloroethyl, tetrahydropyranyl, substituted and unsubstituted phenylalkyl (e.g., benzyl) and substituted derivatives thereof (e.g., alkoxybenzyl, nitrobenzyl), cinnamyl, dialkylaminoalkyl (e.g., dimethylaminoethyl), trimethylsilyl, substituted and unsubstituted amides and hydrazides (e.g., amides and hydrazides of N,N-dimethylamine), 7-nitroindole, hydrazine, N-phenylhydrazine, acyloxyalkyl (e.g., pivaloyloxymethyl, propionyloxymethyl), aroyloxyalkyl (e.g., benzoyloxyethyl), alkoxycarbonylalkyl (e.g., methoxycarbonylmethyl), cyclohexyloxycarbonylmethyl, alkoxycarbonyloxyalkyl (e.g., t-butyloxycarbonyloxymethyl), alkoxycarbonylaminoalkyl (e.g., t-butyloxycarbonylaminomethyl), alkylaminocarbonylaminoalkyl (e.g., methylaminocarbonylaminomethyl), acylaminoalkyl (e.g., acetylaminomethyl), heterocyclylcarbonyloxyalkyl (e.g., 4-methylpiperazinyl-carbonyloxymethyl), dialkylaminocarbonylalkyl (e.g., dimethylaminocarbonyl-methyl), (5-(lower alkyl)-2-oxo-1,3-dioxolen-4-yl)alkyl (e.g., (5-t-butyl-2-oxo-1,3-dioxolen-4-yl)methyl), and (5-phenyl-2-oxo-1,3-dioxolen-4-yl)alkyl (e.g., (5-phenyl-2-oxo-1,3-dioxolen-4-yl)methyl).

Exemplary amine and/or amide protecting groups include, but are not limited to, acyl (e.g., formyl, acetyl, chloroacetyl, trichloroacetyl, o-nitrophenylacetyl, o-nitrophenoxy-acetyl, trifluoroacetyl, acetoacetyl, 4-chlorobutyryl, isobutyryl, o-nitrocinnamoyl, picolinoyl, acylisothiocyanate, aminocaproyl, benzoyl), acyloxy (e.g., methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (Boc), 1,1-dimethyl-propynyloxycarbonyl, benzyloxycarbonyl (Cbz), p-nitrobenzyloxycarbonyl, 2,4-dichloro-benzyloxycarbonyl), 9-xanthenyl, and trityl. Additional exemplary amide protecting groups include, but are not limited to, o-nitrocinnamoyl, picolinoyl, aminocaproyl, benzoyl, acyloxy (e.g., methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (Boc), 1,1-dimethyl-propynyloxycarbonyl, benzyloxycarbonyl (Cbz), p-nitrobenzyloxycarbonyl, and 2,4-dichloro-benzyloxycarbonyl). Exemplary indole protecting groups include, but are not limited to, formyl (For) and t-butyloxycarbonyl (Boc). Exemplary imidazole protecting groups include, but are not limited to, tosyl (Tos), benzyloxymethyl (Bom), trityl (Trt), and t-butyloxycarbonyl (Boc). Exemplary guanidinium protecting groups include, but are not limited to, 2,2,4,6,7-pentamethyl-2,3-dihydrobenzofuran-5-sulfonyl (Pbf) and t-butyloxycarbonyl (Boc).

Exemplary hydroxyl protecting groups include, but are not limited to, unsubstituted or substituted alkyls (e.g., t-butyl, allyl, benzyl, methoxymethyl, tetrahydropyranyl, o-nitrobenzyl), silyl (e.g., t-butyldimethylsilyl (TBDMS), t-butyldiphenylsilyl (TBDPS)), acyl (e.g., acetyl, benzoyl, pivaloyl). Exemplary thiol protecting groups include, but are not limited to, p-methylbenzyl (Meb), acetamidomethyl (Acm), and trityl (Trt).

The artisan will appreciate that there are various resins available for building the peptides presented herein. For example, Sieber and Rink amide resins are well known to the artisan for preparing peptides disclosed herein; however, alternative resins may be selected for the preparation of peptides described herein. Resins such as, for example, but not limited to, 2-CTC and related resins may be used to prepare a target peptide, followed by a C terminus amidation step.

The Solid Phase Peptide Synthesis (SPPS) builds described herein are accomplished using standard fluorenylmethyloxycarbonyl chloride (Fmoc) peptide chemistry techniques employing sequential couplings with an automated peptide synthesizer. In some embodiments, the resin is swelled with DMF then deprotected using 20% piperidine (Pip)/DMF (3×30 min). In some embodiments, subsequent Fmoc deprotections use 20% Pip/DMF 3×30 min treatments and 4×30 min treatments are used for more difficult couplings. In some embodiments, after deprotection, the resin is washed with 5×2 min, 10 volume DMF washes. In some embodiments, amino acid pre-activation uses diisopropylcarbodiimide (DIC)/ethyl cyanohydroxyiminoacetate (OXYMA) DMF solutions at room temperature for 30 min. In some embodiments, coupling of the activated amino acid to the resin bound peptide occurs for a specified time for each individual amino acid. In some embodiments, solvent washing with 5×2 min 10 volumes DMF is performed after each coupling. In some embodiments, for isolation of the final product, the resin bound product is washed 5×2 min with 10 volume DCM to remove DMF. In some embodiments, the resin is washed with 2×2 min 10 volume IPA to remove DCM, washed 5×2 min 10 volume methyl-tert-butyl ether (MTBE), then the product is dried at 40° C. under vacuum. In some embodiments, the resin bound product is stored cold (−20° C.). In some embodiments, for analysis, the peptide is cleaved from the resin with an acidic cocktail consisting of trifluoroacetic acid (TFA)/H$_2$O/TIPS (triisopropylsilane)/DTT (dithiothreitol) in the following ratio: (0.93v/0.04v/0.03v/0.03w). In some embodiments, the resin is swelled with DCM (4-5 mL, 3×30 min) and drained. In some embodiments, the cleavage cocktail (4-5 mL) is added to the pre-swelled resin and the suspension is stirred for 2 hr at room temperature. In some embodiments, the solution is filtered then the resin is washed with a small amount of DCM and combined with the cleavage solution. In some embodiments, the resulting solution is poured into 7-10 volumes of cold (0° C.) methyl-tert-butyl ether (MTBE). In some embodiments, the suspension is aged for 30 min at 0° C. then the resulting precipitate is centrifuged and the clear solution is decanted. In some embodiments, the residue is suspended in the same volume of MTBE, and the resulting suspension is again centrifuged and decanted. In some embodiments, after decanting, the clear MTBE solution of the precipitated peptide is dried in vacuo at 40° C. overnight.

As described in the present disclosure, native chemical ligation is a process useful for preparing full length peptides comprising a cysteine or an alanine in the sequence. The process employs a chemoselective reaction of two unprotected peptide segments to produce a transient thioester-linked intermediate. The thioester-linked intermediate rearranges to provide a full-length ligation product having a native peptide bond at the ligation site. The artisan will appreciate that the technique of native chemical ligation can be useful in the chemical synthesis of full-length peptides containing cysteine or alanine.

Enumerated Embodiments

Embodiment 1. A method of preparing tirzepatide or a pharmaceutically acceptable salt thereof, the method comprising: (a) coupling a peptide of SEQ ID NO: 10 to SEQ ID NO: 11 to form a peptide of SEQ ID NO: 12; and (b) deprotecting the peptide of SEQ ID NO: 12 to obtain tirzepatide or a pharmaceutically acceptable salt thereof.

Embodiment 2. The method of Embodiment 1, wherein the peptide of SEQ ID NO: 12 from step (a) is isolated prior to the deprotection step (b).

Embodiment 3. The method of Embodiment 1 or 2, wherein the peptide of SEQ ID NO: 12 from step (a) is washed before the deprotection step (b).

Embodiment 4. The method of Embodiment 1 or 2, wherein the peptide of SEQ ID NO: 12 from step (a) is washed after the deprotection step (b).

Embodiment 5. A method of preparing tirzepatide or a pharmaceutically acceptable salt thereof, the method comprising: (a) coupling a peptide of SEQ ID NO: 13 to SEQ ID NO: 14 to form a peptide of SEQ ID NO: 12; and (b) deprotecting the peptide of SEQ ID NO: 12 to obtain tirzepatide or a pharmaceutically acceptable salt thereof.

Embodiment 6. The method of Embodiment 5, wherein the peptide of SEQ ID NO: 12 from step (a) is isolated prior to step (b).

Embodiment 7. The method of Embodiment 5 or 6, wherein the peptide of SEQ ID NO: 12 from step (a) is washed before the deprotection step (b).

Embodiment 8. The method of Embodiment 5 or 6, wherein the peptide of SEQ ID NO: 12 from step (a) is washed after the deprotection step (b).

Embodiment 9. A method of preparing tirzepatide or a pharmaceutically acceptable salt thereof, the method comprising: (a) coupling a peptide of SEQ ID NO: 15 to SEQ ID NO: 16 to form a peptide of SEQ ID NO: 12; and (b) deprotecting the peptide of SEQ ID NO: 12 to obtain tirzepatide or a pharmaceutically acceptable salt thereof.

Embodiment 10. The method of Embodiment 9, wherein the peptide of SEQ ID NO: 12 from step (a) is isolated prior to step (b).

Embodiment 11. The method of Embodiment 9 or 10, wherein the peptide of SEQ ID NO: 12 from step (a) is washed before the deprotection step (b).

Embodiment 12. The method of Embodiment 9 or 10, wherein the peptide of SEQ ID NO: 12 from step (a) is washed after the deprotection step (b).

Embodiment 13. A compound of SEQ ID NO: 10, or a pharmaceutically acceptable salt thereof, wherein the compound comprises one or more protecting groups.

Embodiment 14. The compound of Embodiment 13, wherein the one or more protecting groups are chosen from Fmoc, Boc, tert-butyl, and trityl groups.

Embodiment 15. The compound of Embodiment 13 or 14, wherein the compound does not comprise one or more of the protecting groups of SEQ ID NO: 10 (i.e., one or more protecting groups are removed from SEQ ID NO: 10).

Embodiment 16. The compound of Embodiment 13 or 14, wherein the compound does not comprise any of the protecting groups of SEQ ID NO: 10 (i.e., all the protecting groups are removed from SEQ ID NO: 10).

Embodiment 17. A compound of SEQ ID NO: 13, or a pharmaceutically acceptable salt thereof, wherein the compound comprises one or more protecting groups.

Embodiment 18. The compound of Embodiment 17, wherein the one or more protecting groups are chosen from Fmoc, Boc, tert-butyl, and trityl groups.

Embodiment 19. A compound of SEQ ID NO: 14, or a pharmaceutically acceptable salt thereof, wherein the compound comprises one or more protecting groups.

Embodiment 20. The compound of Embodiment 19, wherein the one or more protecting groups are chosen from Fmoc, Boc, tert-butyl, and trityl groups.

Embodiment 21. A compound of SEQ ID NO: 15, or a pharmaceutically acceptable salt thereof, wherein the compound comprises one or more protecting groups.

Embodiment 22. The compound of Embodiment 21, wherein the one or more protecting groups are chosen from Fmoc, Boc, tert-butyl, and trityl groups.

Embodiment 23. The compound of Embodiment 21 or 22, wherein the compound does not comprise one or more of the protecting groups of SEQ ID NO: 15 (i.e., one or more protecting groups are removed from SEQ ID NO: 15).

Embodiment 24. The compound of Embodiment 21 or 22, wherein the compound does not comprise any of the protecting groups of SEQ ID NO: 15 (i.e., all the protecting groups are removed from SEQ ID NO: 15).

Embodiment 25. A compound of SEQ ID NO: 16, or a pharmaceutically acceptable salt thereof, wherein the compound comprises one or more protecting groups.

Embodiment 26. The compound of Embodiment 25, wherein the one or more protecting groups are chosen from Fmoc, Boc, tert-butyl, and trityl groups.

Embodiment 27. The compound of Embodiment 25 or 26, wherein the compound does not comprise one or more of the protecting groups of SEQ ID NO: 16 (i.e., one or more protecting groups are removed from SEQ ID NO: 16).

Embodiment 28. The compound of Embodiment 25 or 26, wherein the compound does not comprise any of the protecting groups of SEQ ID NO: 16 (i.e., all the protecting groups are removed from SEQ ID NO: 16).

Embodiment 29. A process of preparing a compound of formula (I):

wherein PG is a protecting group, the process comprising:
(a) contacting a compound of formula (Ia) and diisopropylethylamine

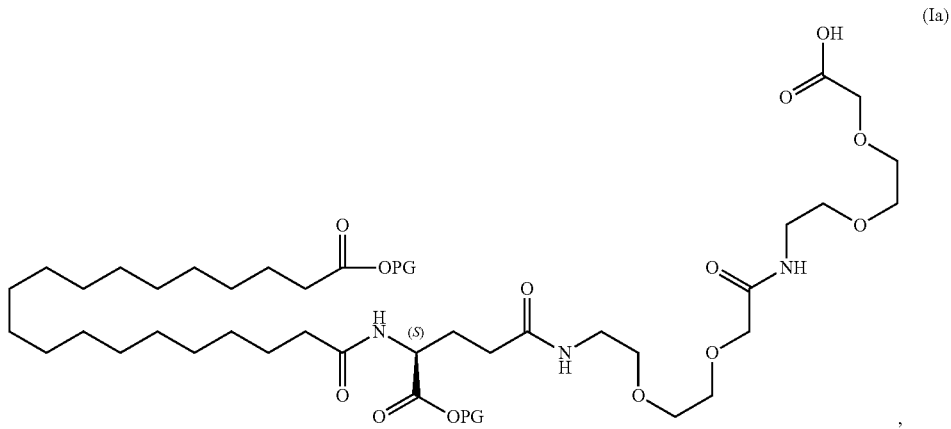

(b) contacting the product of step (a) with 2-(5-norbornene-2,3-dicarboximido)-1,1,3,3-tetramethyluronium tetrafluoroborates in DMF; and
(c) adding a compound of formula (Ib) to the mixture of (b),

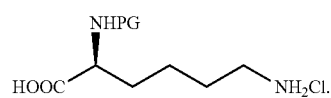

Embodiment 30. The process of Embodiment 29, wherein the protecting group is chosen from Boc and Fmoc.

Embodiment 31. The process of Embodiment 29 or 30, wherein the protecting group is Fmoc.

Embodiment 32. The process of any one of Embodiments 29 to 31, wherein the process is conducted using continuous flow.

Embodiment 33. The process of any one of Embodiments 29 to 32, wherein the process is carried out in flow reactor.

Embodiment 34. The method of any one of Embodiments 1-12, wherein the method includes filtering the tirzepatide or pharmaceutically acceptable salt thereof under one or more of the following conditions: (i) a temperature from 10 to 34° C., optionally about 20° C.; (ii) a turbulent flow/crossflow velocity from 1.94 to 2.46 m/s, optionally about 2.2 m/s; (iii) a laminar flow/shear rate from $2.1 \times 10^3$ to $2.7 \times 10^3$ 1/s, optionally about $2.4 \times 10^3$ 1/s; (iv) a primary product concentration from 32.8 to 47.2 mg/mL, optionally about 40 mg/mL; and (v) a secondary product concentration from 37 to 53 mg/mL, optionally about 45 mg/mL.

EXAMPLES

Example 1

Method 1: Side Chain (SC100) Synthesis Using LPPS Techniques

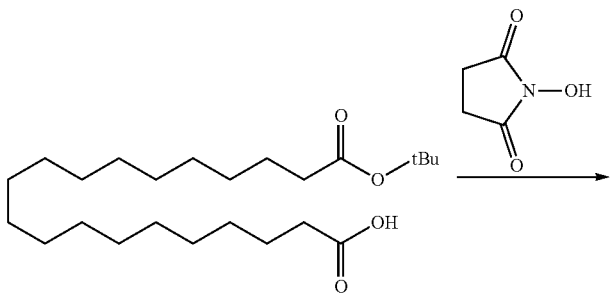

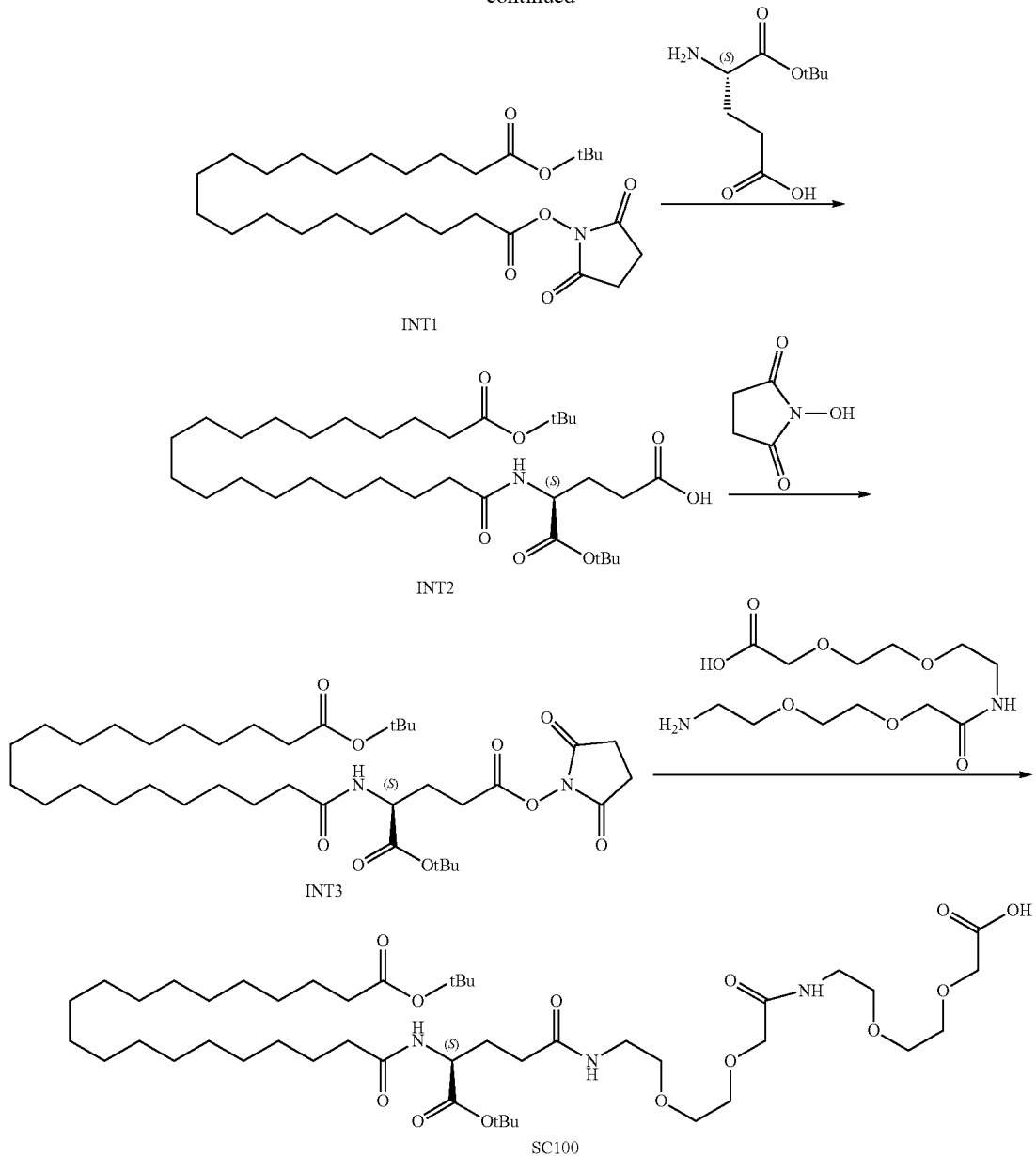

Eicosanedioic acid, mono(1,1-dimethylethyl)ester (15.0 kg, limiting reagent) and N-hydroxysuccinimide (1.2 eq) were dissolved in ethyl acetate at 27° C. A solution of DCC (1.25 eq.) in ethyl acetate was added and the reaction was stirred for 24 hr at 22° C. The resulting DCU by-product was filtered off and then the organic phase was extracted three times with a 5% NaCl aq. solution. After extraction, the organic phase was concentrated, co-evaporated with isopropanol, and then crystallized by addition of heptane. After filtration, the filter cake was rinsed with heptane and dried at 25° C. to afford 17.0 kg of INT1 in 87% yield and 99% purity.

H-Glu-OtBu (7.7 kg, 1.1 eq) was dissolved in DCM (54 L) at 20° C., then a solution of TMSA (11.3 kg) dissolved in DCM (7 L) was added, and the reaction mixture was stirred for 1 hr at 40° C. An INT1 (17.0 kg) DCM solution was added at room temperature and stirred for 8 hr. After the reaction was complete, DCM was exchanged to ethyl acetate by distillation. The organic phase was washed three times with a 2% aq. $KHSO_4$/NaCl aqueous solution and then washed 4 times with a 2% NaCl aqueous solution. After separation and removal of the aqueous phases, the organic phase was concentrated with isopropanol, diluted with isopropanol, and then crystallized by addition of water. After filtration, the filter cake was washed with a mixture of water/isopropanol, and then dried at 30° C. to produce 17.3 kg of INT 2 in 86% yield and 99% purity.

INT 2 (17.3 kg) and N-hydroxysuccinimide (4.1 kg, 1.2 eq) were dissolved in ethyl acetate (336 kg) at 27° C. A solution of DCC (8.33 kg, 1.25 eq) in ethyl acetate was added and the reaction was stirred for 24 hr at 22° C. The resulting DCU by-product was filtered off. The organic phase was concentrated, co-evaporated with isopropanol, and then crystallized by cooling the isopropanol solution (~125 L). After, the filter cake was rinsed with cold isopropanol and dried at 25° C. to afford 16.3 kg INT 3 with 81% yield and 96% purity.

17-Amino-10-oxo-3,6,12,15 tetraoxa-9-aza heptadecanoic acid (AEEA2) (8.1 kg, 26.3 mol) was suspended in DCM (54 L) at 22° C., a TMSA (7.68 kg, 59.9 mol) solution in DCM (6.2 L) was added, and then the reaction mixture was stirred for an hour at 40° C. INT 3 (16 kg) in DCM (31 L) was suspended at 35° C. and added to the TMS-protected (AEEA2) mixture at 22° C. The reaction was stirred for 12 hr, and after reaction completion the mixture was concentrated, and then exchanged to ethyl acetate. The organic phase was washed three times with a 2% aq. KHSO$_4$/NaCl aqueous solution (~200 L), and then washed 4 times with a 2% NaCl aqueous solution (~200 L) to a target pH of 4.5. The organic phase was concentrated and exchanged to acetonitrile. The acetonitrile solution was cooled to −20° C. and then the resulting suspension was aged for 15 hr at −20° C. The mixture was filtered, the filter cake was rinsed with cold acetonitrile and then dried at <0° C. to afford 18.4 kg of SC100 (88% yield) with 96% purity. The overall yield was 53%.

Method 2: Side Chain SC100 Synthesis Using a Peptide Synthesizer (SPPS Techniques)

Alternatively, SC100 may be prepared using a peptide synthesizer when only amide coupling reactions are needed. Standard coupling procedures are utilized.

Standard coupling conditions comprised 0.133 M, 2.0 equiv HATU and 5.0 equiv DIEA at ambient temperature for 3 hours, followed by deprotection using 3×15 min, 20% piperidine/DMF. Resin charging comprised FmocNH-AEEA on 2-CTC resin (0.99 mmol/g) using 1.01 g in each of the parallel reactions. An automatic program was used that included a DMF swell, followed by addition of Pip/DMF; a DMF wash; and amino acid, DIEA, HATU mix; and DMF wash cycles, followed by drying. The resin was cleaved by stirring the combined lots in 30% HFIP/DCM (240 mL) for 1.5 hours. The resin was filtered, washed, and the solvent was removed from the filtrate in vacuo. The resulting oil was dissolved in acetonitrile and solvent was removed again. This operation provided 30.47 g (146% f theoretical yield) of a viscous yellow oil, containing 52.3 area % desired product by UPLC analysis. The crude product was purified by flash chromatography (500 grams of silica gel, eluted with 85% DCM/10% methanol/5% acetic acid, 38×100 mL fractions collected). The previously chromatographed concentrate (17.94 g) was crystallized to yield 13.4 g (74.7% yield), with a UPLC purity of 91.65 area %.

Method 3 (via Route 1 or Route 2): Side Chain SC100 Synthesis:

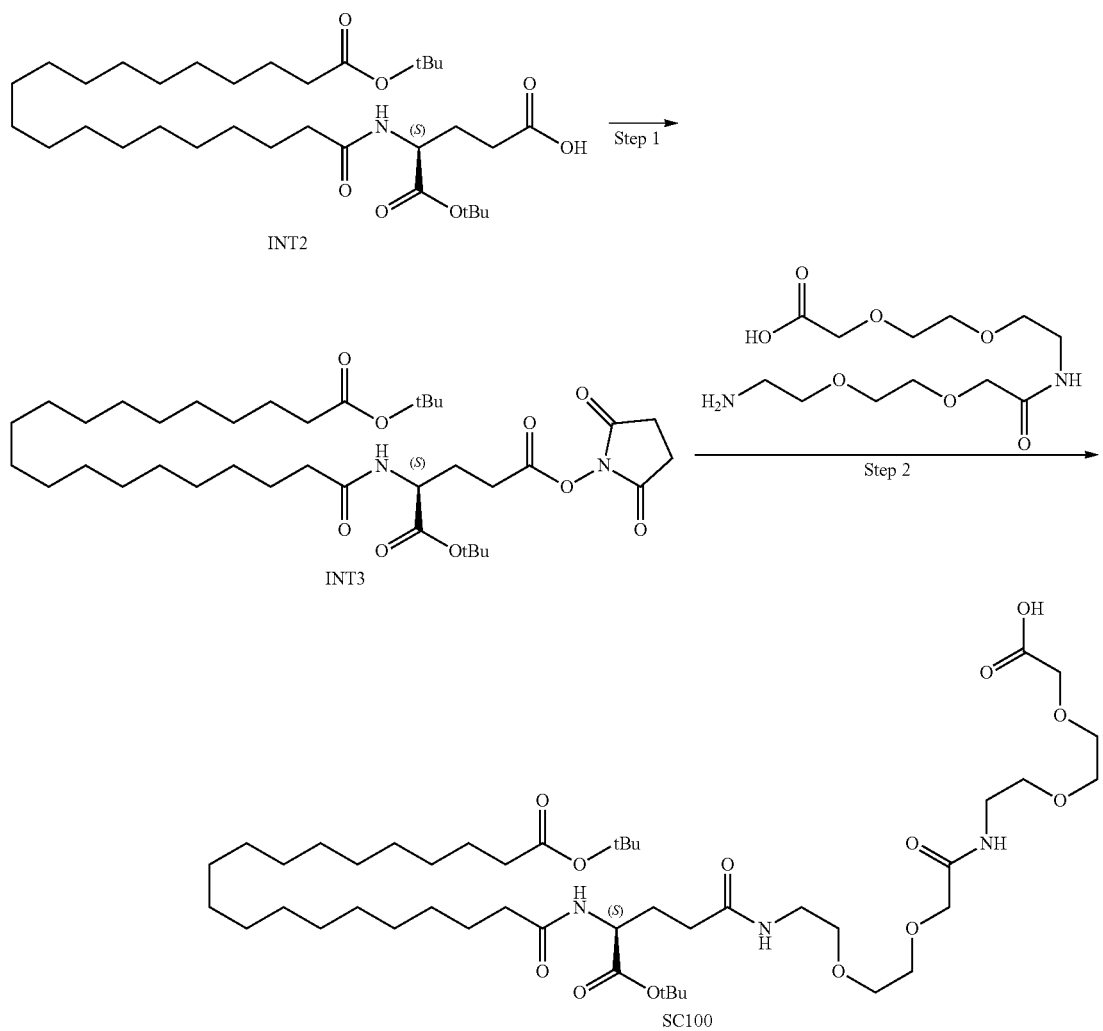

Route 1:

Step 1: To a mixture of dichloromethane, INT1 and N-hydroxysuccinimide (HOSu), 1-ethyl-3-(3-dimethylaminopropyl)carbodiimide (EDCI) was added over 1.5 to 3 hours. The reaction was stirred at 15° C. to 25° C. for 2 to 5 hours. Additional HOSu (target 0.09 eq) and EDCI (target 0.09 eq) may be charged, and the reaction stirred an additional 2 to 5 hours if the reaction is incomplete. Upon reaction completion, the reaction was concentrated via distillation to remove dichloromethane. Following this, two cycles of acetonitrile addition, followed by a concentration step were performed. After the second concentration, water was added to precipitate the product. The slurry was aged for 8 to 16 hours at 20° C. to 30° C. before it was filtered and washed with a 2:1 mixture of water:acetonitrile. The wet cake was transferred to a reactor and acetonitrile was charged. The reactor was heated to 25° C. to 35° C. for 1 to 2 hours. The temperature was then lowered to −5° C. to 5° C. over 6 to 7 hours and aged for 30 min to 1 hour. The precipitated slurry was thermocycled between −5° C. to 5° C. and 15° C. to 25° C. Filtration occured at −5° C. to 5° C. and the wet cake was washed with cold acetonitrile. Following this, the product was dried under vacuum at 25° C. to 35° C.

Step 2: A mixture consisting of 17-amino-10-oxo-3,6,12,15 tetraoxa-9-aza heptadecanoic acid (AEEA2), dichloromethane and N-(trimethylsilyl)acetamide (TMSA) was stirred at 35° C. to 45° C. for 2 to 4 hours. Following this, the temperature was adjusted to 30° C. to 35° C. and INT2 was charged. The reaction was stirred at 30° C. to 35° C. for 12 to 48 hours. Upon reaction completion, the mixture was cooled to 10° C. to 20° C. and washed with two aqueous washes of 3% KHSO$_4$ and 25% NaCl followed by an aqueous wash of 25% NaCl. After removal of the aqueous layer, the organic layer was concentrated via distillation to remove dichloromethane. Following this, two cycles of acetonitrile addition, followed by a concentration step, were performed. The solution was then cooled to −25° C. to −20° C. to precipitate the product. The slurry was aged for 10 to 16 hours, filtered, washed with cold acetonitrile, and dried under vacuum at −20° C. for 2 to 6 hours. The cake was then warmed to −15° C. to −5° C. and dried under vacuum for 6 to 10 hours before warming the cake to −5° C. to 3° C. and continuing to dry under vacuum. Following drying completion, DMF was charged to dissolve the solid product and achieve a 20 to 30% w/w SC100 solution in DMF.

Route 2:

Step 1: To a mixture of acetonitrile, 4-dimethylaminopyridine (DMAP), and INT1, N,N-disuccinimidyl carbonate (DSC) was added at a target temperature of 35° C. for a reaction target time of 3 hours. Following reaction completion, the solution was cooled to −10° C. to precipitate the product. The slurry was thermocycled between −10° C. and 20° C. Following the temperature cycles, the slurry was filtered and dried at 25° C.

Step 2: A mixture consisting of acetonitrile (ACN), 17-amino-10-oxo-3,6,12,15 tetraoxa-9-aza heptadecanoic acid (AEEA2), and N-methyl-N-trimethylsilylacetamide (N-Me-N-TMSA) was allowed to stir at a target temperature setpoint of 25° C. for two hours. Following this, INT2 was charged to the mixture, and the reaction proceeded at a target temperature setpoint of 25° C. for four hours. Following reaction completion, ethyl acetate (EtOAc) was added to the mixture, followed by two washes of aqueous 2% potassium bisulfate/1% NaCl and two washes of aqueous 2% NaCl solutions. After removal of the aqueous layer of the reaction solution, EtOAc was removed via distillation. Following EtOAc removal, ACN was charged and removed by distillation four times. The solution is then cooled to a target temperature of −20° C. to effect precipitation. The slurry was aged for 15 hours, and the product was filtered and washed with cold ACN. The solids are initially dried under vacuum at −19° C. to −13° C., then the temperature was increased to −10° C., and lastly −3° C. to further dry the product. Following drying completion, DMF was charged to dissolve the solid product and achieve a 20 to 30% w/w SC100 solution in DMF.

Step 3 (Route 1 and Route 2):

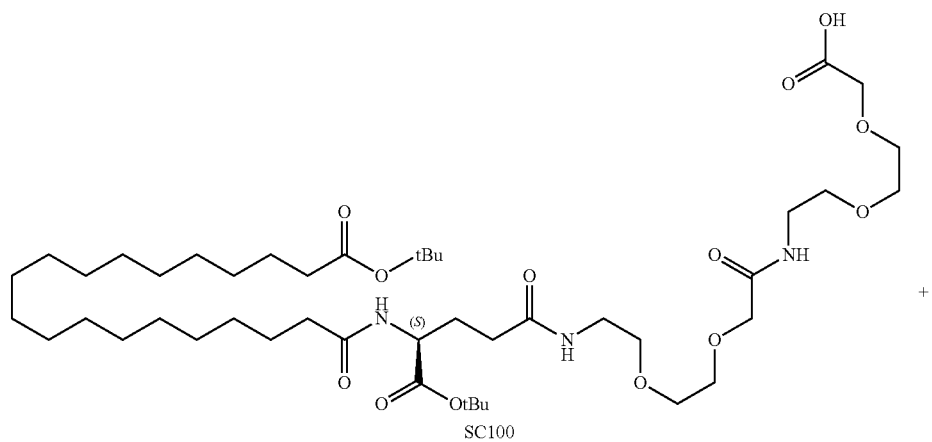

SC100

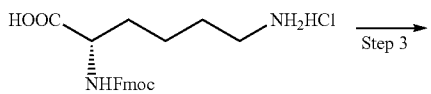

Step 3

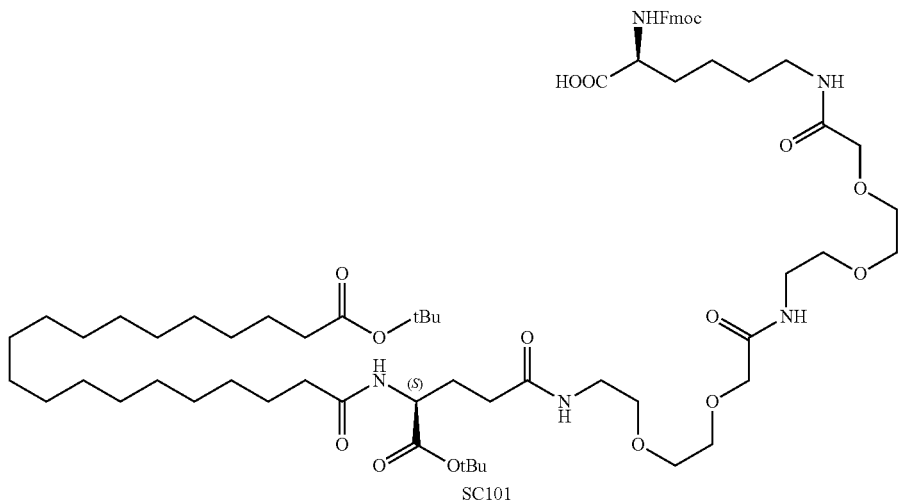

SC101

Step 3: A solution of SC100 in DMF was combined with diisopropylethylamine (DIPEA) in a flow reactor. The solution was passed through an in-line mixer and combined with a solution of TNTU in DMF. After a target residence time of thirty (30) minutes, the resulting activated ester intermediate was mixed in-line with a solution of (((9H-fluoren-9-yl) methoxy)carbonyl)-L-lysine hydrochloride (Fmoc-Lys-OH·HCl) in DMF. Following a target residence time of fifteen (15) minutes, the reaction was complete, and 2-methyltetrahydrofuran (Me-THF) and aqueous sodium chloride/potassium hydrogen sulfate (aq. NaCl/KHSO$_4$) were mixed in-line to quench the reaction and create a bi-phasic mixture. A batch extractive work-up with aqueous NaCl/KHSO$_4$, Me-THF and DMF was followed by azeotropic distillation to remove Me-THF and water. Finally, DMF was charged to achieve a 20-30% w/w SC101 solution in DMF. SC101 is a species of a compound of formula (I) of the present disclosure.

Example 2

Synthesis of Fmoc-Hydrazine-CTC Resin (Preparation 1)

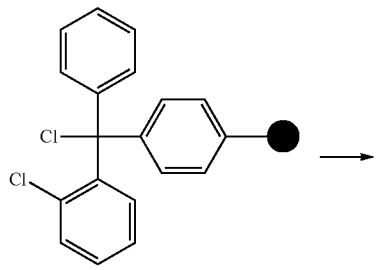

2-Chlorotrityl chloride
(2-CTC) resin

→

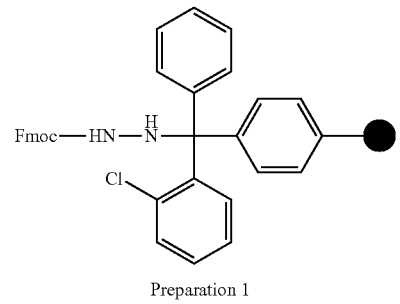

Preparation 1

2-CTC resin (10.7 g, 17.7 mmol) was swollen in 100 mL DCM for 20 min at 0° C. 9-fluorenylmethyl carbazate (15.6 g, 61.4 mmol, 3.5 equiv) was dissolved in 210 mL of 2:1 DMF:DCM. DIEA (31 mL, 178 mmol, 10.1 equiv) was added to the 9-fluorenylmethyl carbazate solution. This solution was then slowly added to the resin at 0° C. It was stirred at 0° C. for about an hour and allowed to warm up to room temperature. The reaction mixture was stirred over 16 hours at room temperature. Methanol (10 mL) was then added to quench the remaining 2-CTC resin and stirred for 15 min. The resin was rinsed with 200 mL DMF, followed by DMF (2×100 mL), water (3×100 mL), DMF (3×100 mL), methanol (3×100 mL), and finally with DCM (3×100 mL). The resin was dried in a vacuum oven at 27° C. for 16 hours. The resin loading was measured to be 0.74 mmol/g by quantitative NMR.

Example 3

Synthesis of Peptide Hydrazide Fragment 1-17: (SEQ ID NO: 2)

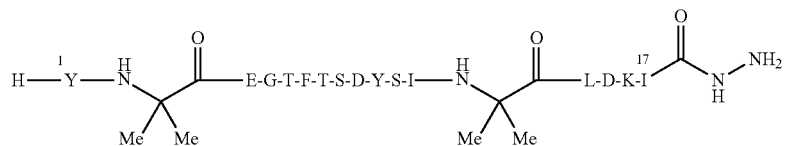

SEQ ID NO: 2

Hydrazine-CTC resin (1.01 g, loading value: 0.65 mmol/g) was taken in a 40 mL reactor vessel and swollen with 3×4 mL DCM (30 s each) followed by 2×10 mL DMF (20 min each) on a peptide synthesizer. Fmoc-Ile-OH (0.919 g, 2.60 mmol, 4 equiv) and HBTU (0.99 g, 2.61 mmol, 4 equiv) were dissolved in 7 mL of DMF. DIPEA (0.91 mL, 5.22 mmol, 8 equiv) was added to the amino acid solution and the volume was made up to 10 mL with DMF. The activated amino acid solution was added to the resin. The slurry was allowed to mix with nitrogen for 8 hours. After 8 hours, the resin was washed with 5×10 mL DMF and 5×10 mL DCM and dried for 12 hours. The loading of the resulting resin was measured to be 0.54 mmol/g by quantitative NMR. 0.91 g of this resin was used for the peptide hydrazide fragment 1-17 (SEQ ID NO: 2) synthesis.

Deprotection was undertaken using 4×9 mL of a 20% v/v piperidine in DMF, for 30 minutes each.

Amino acid couplings were carried out using 3 equivalents of amino acid, 3 equivalents of OXYMA and 3.3 equivalents of DIC. The resin was washed with 5×9 mL DMF with 1 min $N_2$ mix after each coupling and the final iteration of deprotection. At the end of the peptide hydrazide synthesis, the resin was washed with DCM with $N_2$ mixing. The resin was dried on the synthesizer.

Deprotection and Cleavage: 25 mL of the cleavage cocktail made with 5% w/v dithiothreitol (DTT), 2.5% v/v water, 2.5% v/v triisopropylsilane (TIPS) and 90% trifluoroacetic acid (TFA) was added to the dried resin (2.37 g) and mixed for 3 hours on a rotary mixer. The resin was filtered and washed with 2×2.5 mL TFA. The filtrate was poured into 175 mL cold MTBE and the peptide precipitated out immediately. The filtration flask was washed with 2×2.0 mL TFA and poured into the cold MTBE. It was cooled down to −20° C. for half an hour and then centrifuged. The peptide precipitate was then washed twice with 150 mL MTBE and centrifuged. The peptide precipitate was dried in a vacuum oven at 27° C. for 16 hours. A 1.25 g sample of the crude peptide hydrazide fragment 1-17 (SEQ ID NO: 2) was obtained after drying [Expected (mass+2H$^+$)/2=968.4883, observed (mass+2H$^+$)/2=968.4879].

Example 4

Synthesis of Cysteine-18 Fragment 18-39, with SC100 Attached: (SEQ ID NO: 3)

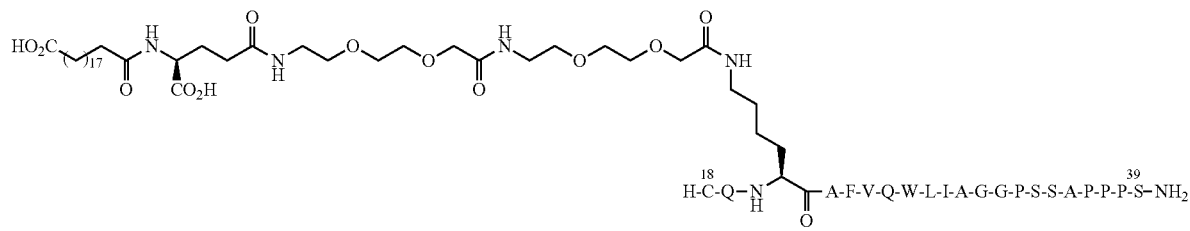

SEQ ID NO: 3

About 0.62 mmol of SEQ ID NO: 3 was synthesized on Sieber amide resin by standard SPPS protocols. Fmoc-Lys (ivDde)—OH was used for orthogonal deprotection and lysine acylation.

Deprotection of ivDde: Hydrazine monohydrate (64% w/w) (1.98 g, 25.3 mmol) was diluted to 24.4 g with DMF and 20 g was added to the resin. The slurry was allowed to stir with a nitrogen stream and washed with 5×9 mL DMF after about two hours. It was repeated once more.

2-[2-[2-[2-[[2-[2-[2-[[(4S)-5-tert-butoxy-4-[(20-tert-butoxy-20-oxo-icosanoyl)amino]-5-oxo-pentanoyl]amino]ethoxy]ethoxy]acetyl]amino]ethoxy] ethoxy]acetic acid (1094.4 mg, 1.252 mmol, 2 equiv) was dissolved in 10 mL of anhydrous DMF. TNTU (506.9 mg, 1.360 mmol, 2.2 equiv) and DIEA (0.24 mL, 1.4 mmol, 2.2 equiv) were added to it. The volume was made up to 15 mL with anhydrous DMF. It was allowed to mix for 30 min on a rotary mixer. The activated ester of SC100 was then added to the resin and allowed to mix for 12 hours with nitrogen stream. After 12 hours, the solution was drained and the resin was washed with 5×10 mL DMF and 7×10 mL DCM with 1 min $N_2$ mix. The resin was dried for 8 hours on the synthesizer.

Deprotection and Cleavage: 20 mL of the cleavage cocktail made with 5% w/v dithiothreitol (DTT), 2.5% v/v water, 2.5% v/v triisopropylsilane (TIPS) and 90% trifluoroacetic acid (TFA) was added to the dried resin (2.42 g) and mixed for 3 hours on a rotary mixer. The resin was filtered and washed with 2×2.0 mL TFA. The filtrate was poured into 200 mL cold MTBE and the peptide precipitated out immediately. The filtration flask was washed with 2×2 mL TFA and was poured into the cold MTBE. It was cooled down to −20° C. for 30 min and then centrifuged. The peptide precipitate was washed twice with 240 mL MTBE and centrifuged. The peptide precipitate was dried in a vacuum oven at 27° C. for 14 hours. 1.853 g of the crude SEQ ID NO: 3 was obtained after drying. It was purified by RP-HPLC on a Kromasil 100-10-C8 10 μm column (30 mm×250 mm) at ambient temperature with a linear gradient of 30-55% acetonitrile in water over 25 min after 15% acetonitrile in water for the first 5 min and a constant 0.10% TFA over 30 min. 1.28 g of the purified SEQ ID NO: 3 was obtained [Expected (mass+2H$^+$)/2=1470.7929, observed (mass+2H$^+$)/2=1470.7885].

Example 5

Synthesis of Thioester Fragment 1-17 (SEQ ID NO: 4) (from Conversion of SEQ ID NO: 2)

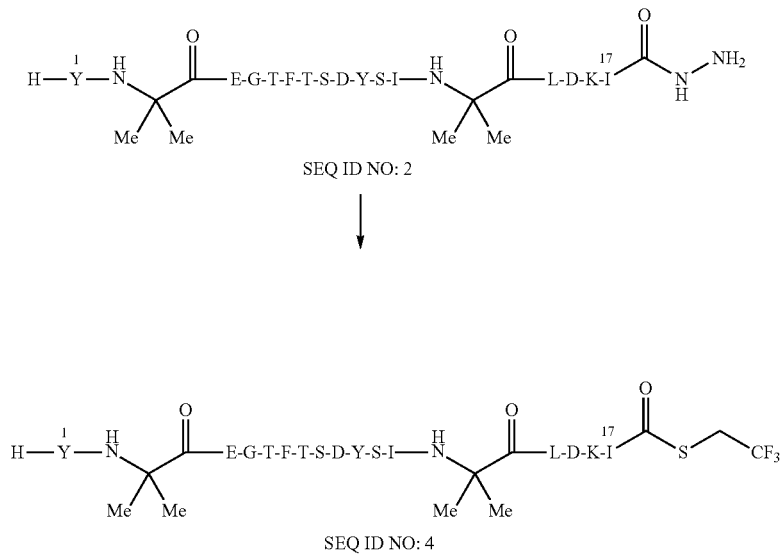

Crude hydrazide fragment 1-17 (SEQ ID NO: 2), 2.422 g, 1.251 mmol) was dissolved in 50 mL of the ligation buffer (6M guanidine hydrochloride and 0.2M sodium hydrogen phosphate monobasic, pH 3.35) and cooled to −15° C. in an acetone-ice bath. 9.4 mL of a 1M sodium nitrite solution (9.4 mmol, 7.5 equiv.) was added to the peptide hydrazide solution and allowed to stir for 20 min at −15° C. Meanwhile, 1 mL of 2,2,2-trifluoroethanethiol (TFET) was made up to 10 mL with ligation buffer (6M guanidine hydrochloride and 0.2M sodium hydrogen phosphate monobasic, pH 7.0). After 20 min, 10 mL of the TFET mixture was added to the peptide hydrazide solution to cause in-situ thiolysis of the peptidyl azide generated from fragment 1-17 (SEQ ID NO: 2).

The pH of the reaction mixture was adjusted to about 6.95 with a 5N sodium hydroxide solution. Thiolysis of the peptidyl azide was allowed to run for 45 min and the volume is made up to 100 mL with the ligation buffer (pH 7.0). The crude thioester mixture was purified by RP-HPLC on a Waters X-Bridge C18 10 μm column (10 mm×250 mm) at ambient temperature with a linear gradient of 25-42% acetonitrile in water over 25 min after 10% acetonitrile in water for the first 2.8 min and a constant 0.1% TFA for the 28 min of purification. This yielded 1.03 g of the TFET thioester SEQ ID NO: 4 [Expected (mass+2H$^+$)/2=1010.4650, observed (mass+2H$^+$)/2=1010.4620].

Example 6

Native Chemical Ligation of Thioester Fragment 1-17 (SEQ ID NO: 4) to Cysteine-18 Fragment 18-39 (SEQ ID NO: 3) to Form Tirzepatide Cysteine-18 Analogue (SEQ ID NO: 5):

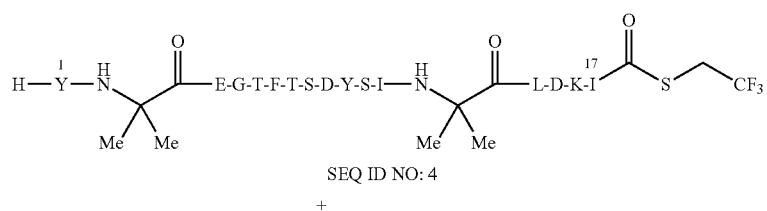

+

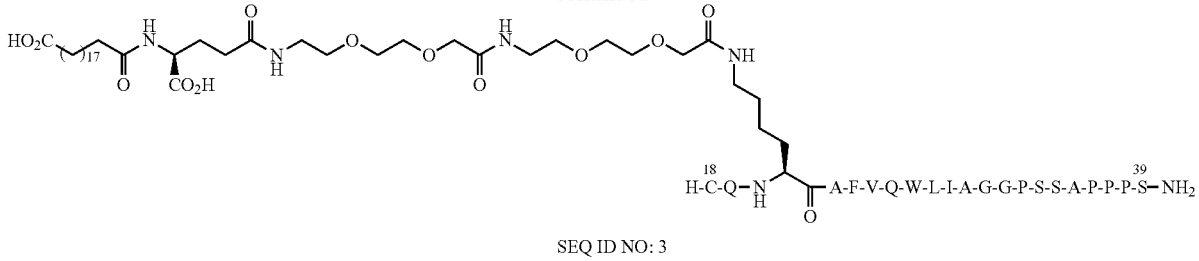

SEQ ID NO: 3

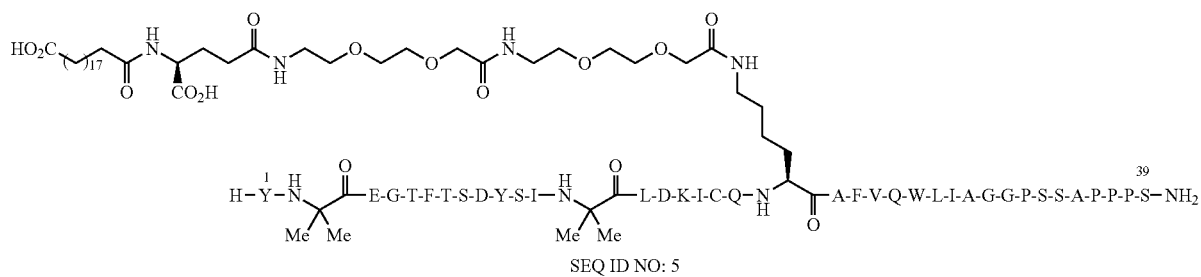

SEQ ID NO: 5

An aqueous solution of 6M guanidine hydrochloride and 0.3 M sodium hydrogen phosphate monobasic (pH 7.0) was the ligation buffer used in native chemical ligation. All solutions were made in this ligation buffer. 350.4 mg (0.174 mmol) of the peptide thioester SEQ ID NO: 4 was dissolved in 50 mL of the ligation buffer. An 8.0 mL portion of 0.5M 4-mercaptophenylacetic acid (MPAA) solution was added to the peptide thioester solution. N-terminal cysteine containing peptide SEQ ID NO: 3, (524.6 mg, 0.178 mmol, 1.03 equiv) was dissolved in 48 mL of the ligation buffer in a 50 mL centrifuge tube. The solution of SEQ ID NO: 3 was added to the thioester solution. The tube was rinsed with 2×8 mL of the ligation buffer (about pH 7.0) and added to the reaction mixture. The pH of the reaction mixture was adjusted to about 7 with a 5N NaOH solution. An 8.0 mL portion of tris(2-carboxyethyl)phosphine (TCEP, 0.5 M, pH 7.0) was added to the reaction mixture and the pH was adjusted again to 7.0 with 0.2 mL of 5N sodium hydroxide solution. The reaction was allowed to stir at room temperature for 24 hours and was then stored in a freezer. An additional 3 mL of 0.5M TCEP solution was added before purification. SEQ ID NO: 5 was purified by RP-HPLC on a Kromasil C18 10 µm column (10 mm×250 mm) at ambient temperature with a linear gradient of 20-50% acetonitrile in water (0.1% acetic acid and titrated to pH 9.0) over 23 min after 10% acetonitrile in water for the first 4 min during the 28 min of purification. About 372 mg (44.3%) of the tirzepatide cysteine analogue SEQ ID NO: 5 was obtained after purification [Expected (mass+3H$^+$)/3=1615.17263, observed (mass+3H$^+$)/3=1615.1686].

Desulfurization:

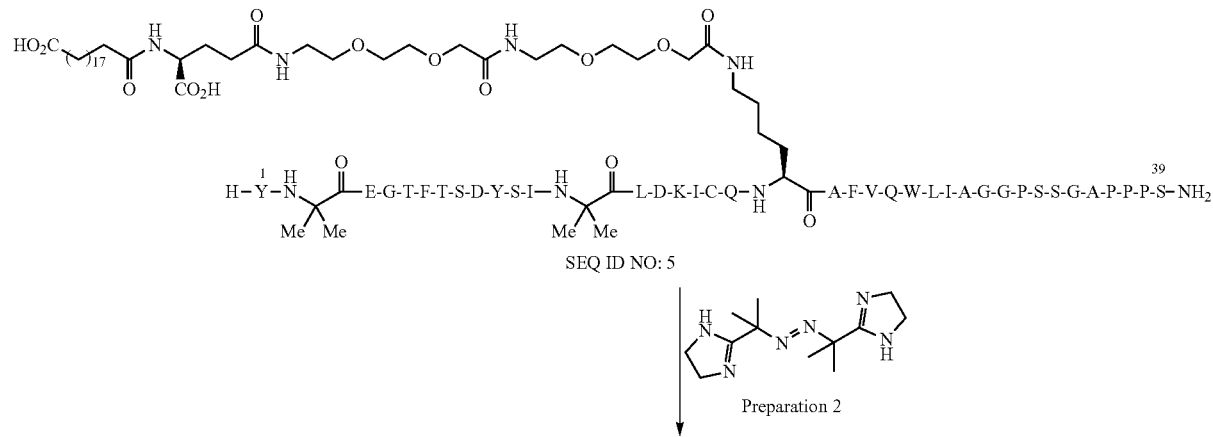

SEQ ID NO: 5

Preparation 2

-continued

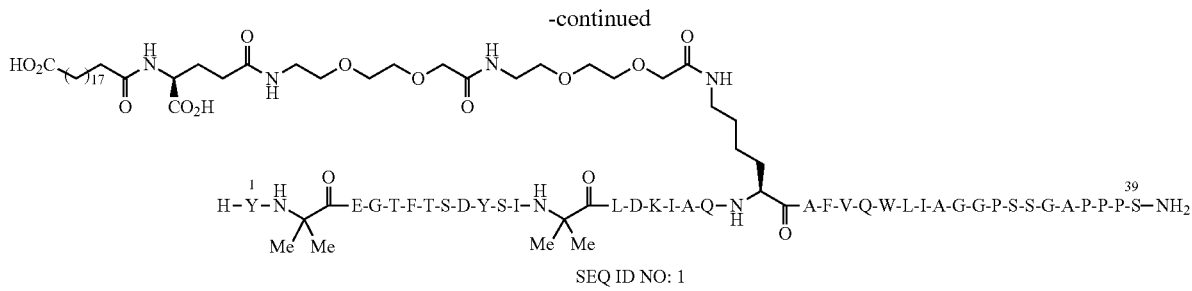

SEQ ID NO: 1

An aqueous solution of 6 guanidine hydrochloride and 0.3 M sodium hydrogen phosphate monobasic (pH 7.0) was the buffer used in desulfurization. All solutions were made in this buffer. 2,2'-Azobis[2-(2-imidazolin-2-yl)propane]dihydrochloride (Preparation 2, 808.2 mg, 2.5 mmol) was dissolved in 10 mL of the buffer and the pH was adjusted to about 7.0 with 5N NaOH. The volume was made up to 15 mL with the buffer. Tirzepatide cysteine analogue SEQ ID NO: 5 (105.2 mg, 0.022 mmol) was dissolved in 30 mL of the buffer and 6 mL of the Preparation 2 solution was added to it. Five mL of 0.3M L-glutathione reduced solution (L-GSH, pH 7.0) and 7.5 mL of 0.5 M TCEP solution (pH 7.0) were added to it. The solution was heated at 44° C. for 4.5 hours, whereby the reaction was found to be complete by UPLC analysis [Expected $(mass+3H^+)/3=1604.5153$, observed $(mass+3H^+)/3=1604.5122$]. The desulfurization yield was calculated by UPLC using a tirzepatide (SEQ ID NO: 1) reference standard. The yield was estimated to be 47%.

Example 7

Synthesis of Hydrazide Fragment 1-20: SEQ ID NO: 6 for 30 min. The activated ester solution of Preparation 3 was added to the resin. The slurry was allowed to mix with nitrogen for 8 hours. After 8 hours, the resin was washed with 5×10 mL DMF, 5×10 mL DCM and dried for 12 hours. The loading of the resulting resin was measured to be 0.26 mmol/g by quantitative NMR. 1.82 g of this resin was used for the peptide hydrazide SEQ ID NO: 6 synthesis.

Deprotection was carried out using 4×9 mL of 20% v/v piperidine in DMF, for 30 minutes each.

Couplings: 3 equivalents of amino acid, 3 equivalents of OXYMA and 3.3 equivalents of DIC were used for amino acid coupling.

The resin was washed with 5×9 mL DMF with 1 min $N_2$ mix after each coupling and the final iteration of deprotection. At the end of the peptide hydrazide synthesis, the resin was washed with 7×10 mL DCM with 1 min $N_2$ mixing. The resin was then dried for about 12 hours on the synthesizer.

Deprotection and Cleavage: 25 mL of the cleavage cocktail made with 5% w/v dithiothreitol (DTT), 2.5% v/v water, 2.5% v/v triisopropylsilane (TIPS) and 90% trifluoroacetic acid (TFA) was added to the dried resin and mixed on a rotary mixer. The resin was filtered, washed with TFA (2×2.5

SEQ ID NO: 6

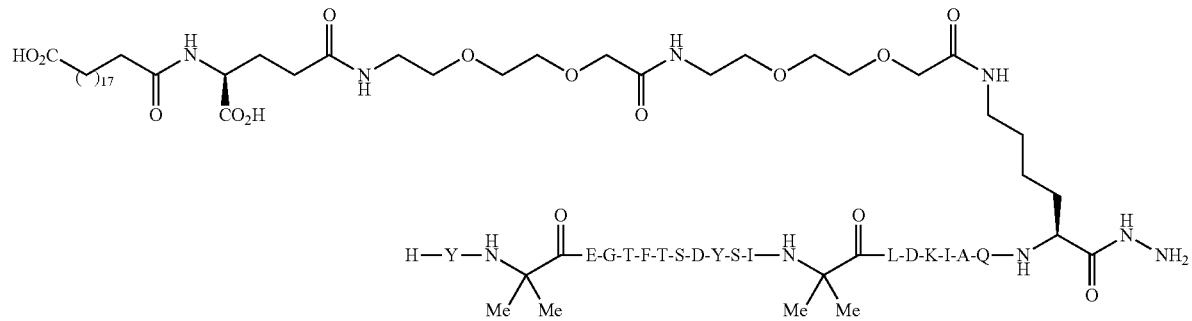

Hydrazine-CTC resin (2.03 g, 1.32 mmol, loading value: 0.65 mmol/g) was taken in a 40 mL reactor vessel and swollen with 3×10 mL DCM (30 s each) followed by 2×10 mL DMF (20 min each) on a Symphony synthesizer. HBTU (1.48 g, 3.90 mmol, 3.0 equiv) was dissolved in 13.1 mL of a (25S,52S)-52-((((9H-fluoren-9-yl)methoxy)carbonyl) amino)-25-(tert-butoxycarbonyl)-2,2-dimethyl-4,23,28,37, 46-pentaoxo-3,32,35,41,44-pentaoxa-24,29,38,47-tetraaza-tripentacontan-53-oic acid (Preparation 3, 365 mg/mL in DMF) solution (3.91 mmol, 3.0 equiv). DIPEA (1.4 mL, 8.04 mmol, 6.1 equiv) was added to the above solution and the volume was made up to 19 mL with DMF. The solution was allowed to mix at room temperature on a rotary mixer mL), and the filtrate was poured into 175 mL of cold MTBE. The filtration flask was washed with TFA (2×2.5 mL) and washings are poured into the cold MTBE. It was cooled down to −20° C. for 30 min and then centrifuged. The peptide precipitate is then washed twice with 150 mL MTBE and centrifuged. The peptide precipitate was dried in a vacuum oven at 27° C. for 16 hours. 1.70 g of the crude peptide hydrazide SEQ ID NO: 6 was obtained after drying. Crude peptide hydrazide, SEQ ID NO: 6 was puriied by RP-HPLC on Waters XSelectCSH C18 10 μm column (10 mm×250 mm) at ambient temperature with a linear gradient of 20-55% acetonitrile in water over 23 min after 10% acetonitrile in water for the first 3 min and a constant 0.1%

TFA for the 28 min of purification. About 110 mg of the partially purified hydrazide SEQ ID NO: 6 was obtained.

Deprotection and Cleavage: 25 mL of the cleavage cocktail made with 5% w/v dithiothreitol (DTT), 2.5% v/v water, 2.5% v/v triisopropylsilane (TIPS) and 90% trifluoroacetic acid (TFA) was added to the dried resin (2.92 g) and mixed on a rotary mixer. The resin was filtered and washed with 2×2.5 mL TFA. The filtrate was poured into 200 mL cold MTBE and the peptide precipitated out immediately. The filtration flask was then washed with 2×2 mL TFA and the washings were poured into the cold MTBE. It was cooled down to −20° C. for 30 min and then centrifuged. The peptide precipitate was then washed twice with 240 mL MTBE and centrifuged. The peptide precipitate was then dried in a vacuum oven at 27° C. for 16 hours. About 1.7 g of the crude 19-mer SEQ ID NO: 8 was obtained.

Example 8

Native Chemical Ligation of Fragment 1-20 (SEQ ID NO: 7) to Cysteine Fragment 21-39 (SEQ ID NO: 8) to Form Tirzepatide Cysteine-21 Analogue (SEQ ID NO: 9)

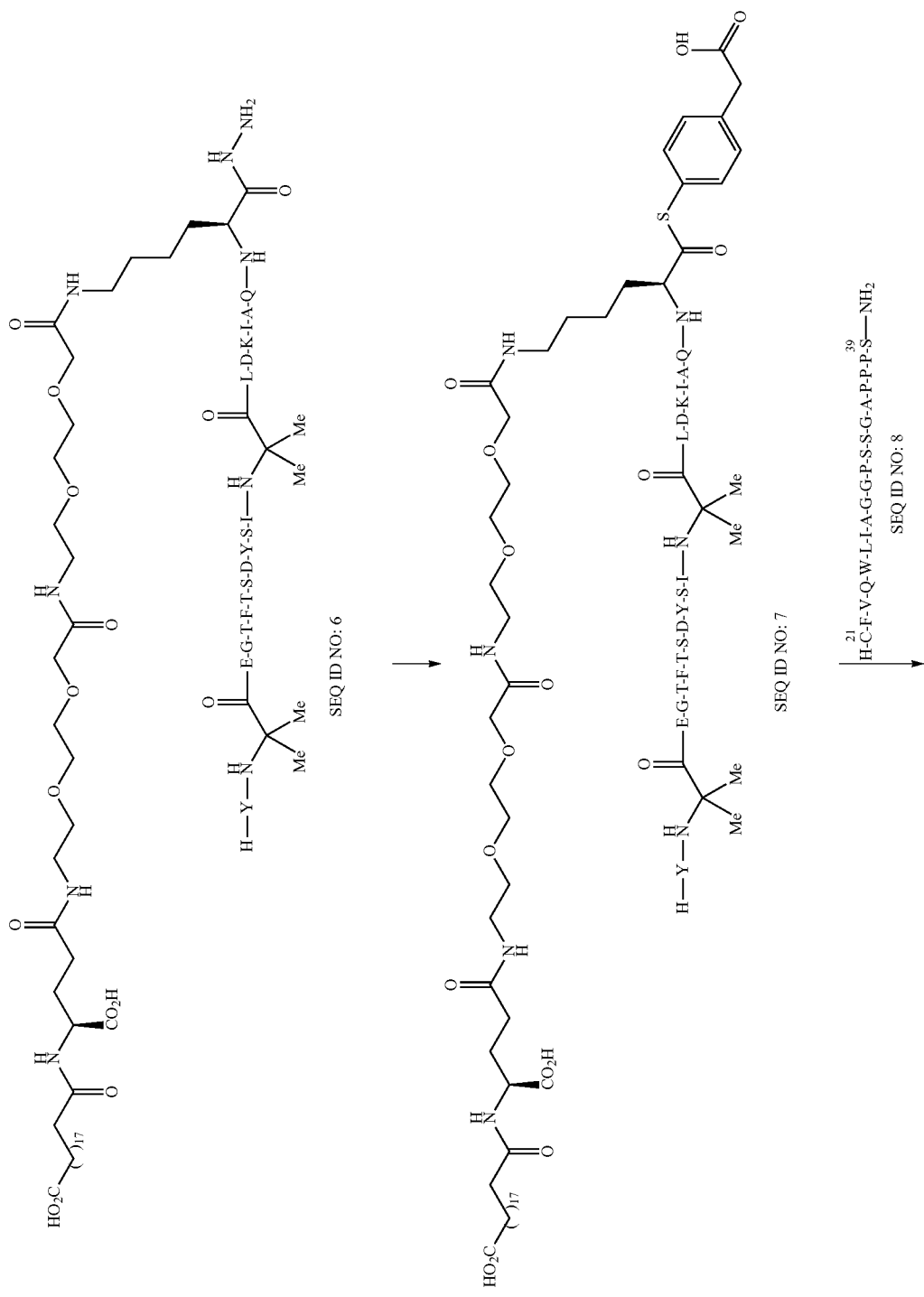

-continued
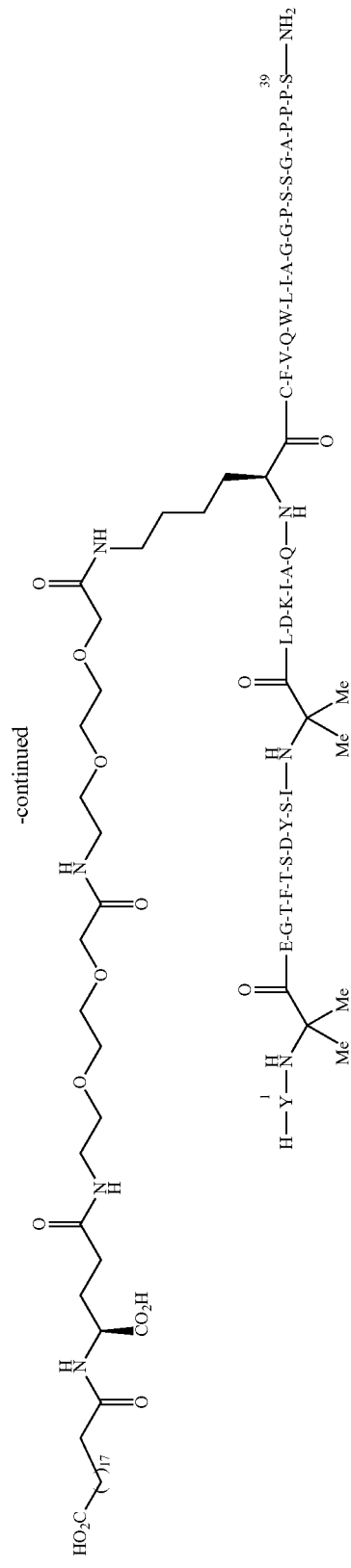
SEQ ID NO: 9

An aqueous solution of 6M guanidine hydrochloride and 0.3 M sodium hydrogen phosphate monobasic (pH 7.0) was the ligation buffer used in native chemical ligation. All solutions were made in this ligation buffer. Partially purified peptide hydrazide (SEQ ID NO: 6, 56 mg, 0.019 mmol) was dissolved in 5 mL of the ligation buffer (6M guanidine hydrochloride and 0.3 M sodium hydrogen phosphate monobasic, pH 3.35) and cooled to −15° C. in an acetone-ice bath. 0.25 mL of a 1M sodium nitrite solution (0.25 mmol, allowed to stir at room temperature for an hour. Tirzepatide cysteine analogue (SEQ ID NO: 9) was observed in the reaction mixture.

Example 9

Native Chemical Ligation: Protected Fragment 1-21 (SEQ ID NO: 10) to Protected Fragment 22-39 (SEQ ID NO: 11)

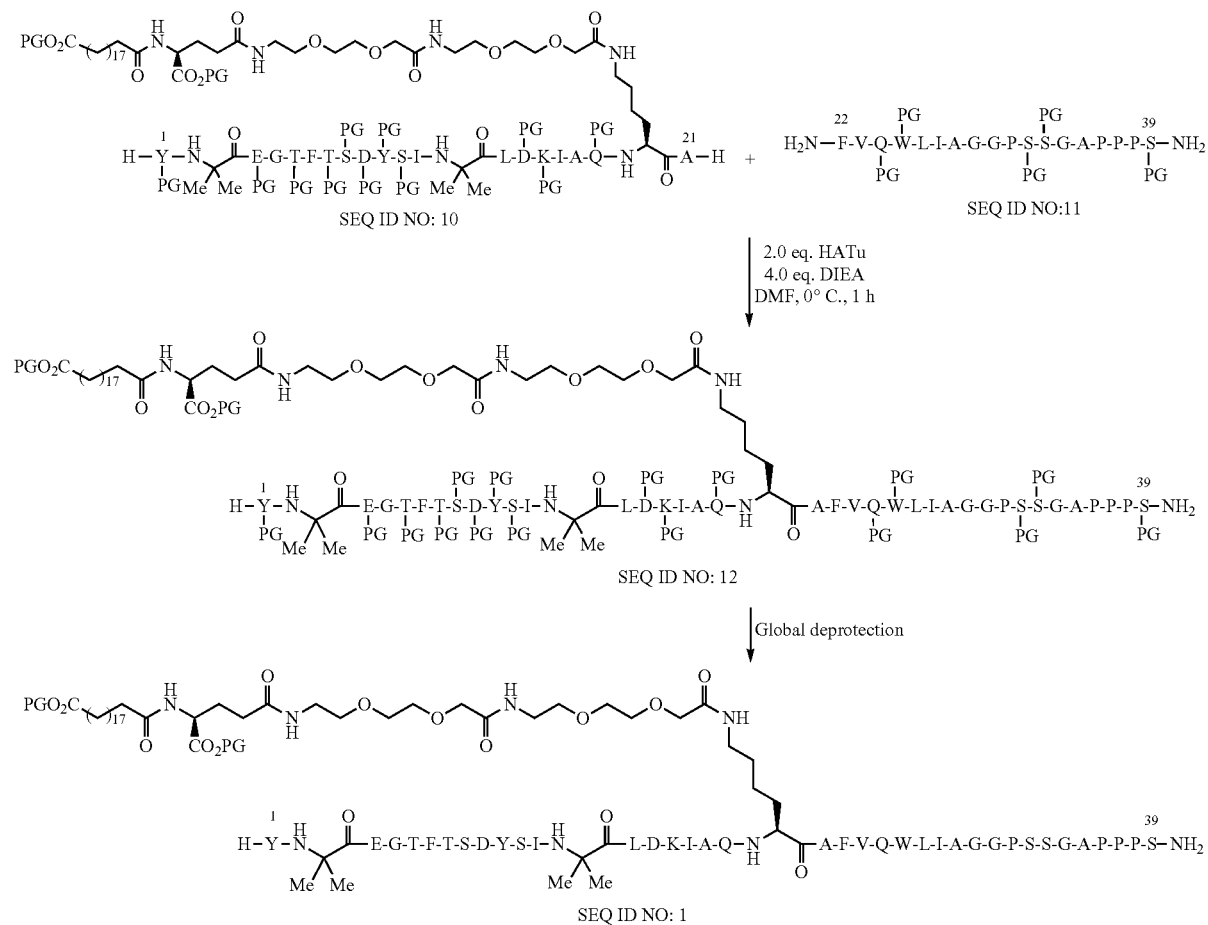

13.2 equiv) was added to the peptide hydrazide solution and it was allowed to stir for 10 min at −15° C. After 10 min, 0.8 mL of 0.5M 4-mercaptophenylacetic acid (MPAA) solution was added to the peptide hydrazide solution to cause in-situ thiolysis of the peptidyl azide generated from SEQ ID NO: 6. The pH of the reaction mixture was adjusted to about 7.0 with 5N sodium hydroxide solution. Thiolysis of the peptidyl azide was allowed to run for 30 min.

About 0.62 mmol of cysteine peptide 21-39 (SEQ ID NO: 8) was synthesized on Sieber amide resin using standard SPPS protocols. N-terminal cysteine containing SEQ ID NO: 8 (26.1 mg, 0.014 mmol, 0.74 equiv) was dissolved in 1 mL of the ligation buffer. The solution of SEQ ID NO: 8 was added to the thioester solution. The vial containing SEQ ID NO: 8 was rinsed with 1 mL of the ligation buffer (pH 7.0) and added to the reaction mixture. After 15 min, 1.0 mL of tris(2-carboxyethyl)phosphine (TCEP, 0.5 M, pH 7.0) was added to the reaction mixture and the pH was adjusted to 7.0 with 5N sodium hydroxide solution. The reaction was Preparation of reagents/substrates: 5 wt % solution of protected fragment 22-39 (SEQ ID NO: 11) (0.04 mmol, 1 equiv, 95.9065 mg, 95.0 wt %) was prepared in DMF (1822.214 uL). Similarly, 5 wt % solution of protected fragment 1-21 (SEQ ID NO: 10) (0.052 mmol, 1.38 equiv, 268.077 mg, 79 wt %) was prepared in DMF (5093.46 uL). 10% (v/v) solution of DIEA (0.084 mmol, 4.2 equiv, 28.64 μL) was prepared in DMF (257.76 uL). 10 wt % solution of HATU (0.04 mmol, 2.0 equiv, 30.418 mg) was prepared in acetonitrile (273.762 uL).

Coupling and isolation: The protected fragment 22-39 (SEQ ID NO: 11) and protected fragment 1-21 (SEQ ID NO: 10) were mixed together, at 0° C. DIEA solution was charged to it at 0° C. followed the addition of HATU solution to the same. The reaction was stirred at 0° C. for 2 h. To it was added 2.0 mL of 17% NaCl/0.5% at 0° C., followed by addition of (2.2 mL) cold water at 0° C. and was stirred for an hour. The off-white precipitate was filtered and washed with water. It was dried under $N_2$ atmosphere in a vacuum oven at 40° C. overnight.

Global deprotection: The above isolated crude API was charged with DCM (1.5 mL/g; 315.75 uL), 20 volumes 92.25% TFA (3.87 mL), 2.5% DTT (0.105 mg), 2.5% water (0.105 mL), and 2.5% TIS (0.105 mL). It was stirred at room temperature for 2 h. It was poured into cold MTBE (30 mL) and kept at 2-4° C. for 30 minutes. It was then centrifuged at 3000 rpm for 3 minutes. The solid precipitate was washed with 2×30 mL MTBE and centrifuged each time. It was dried at 40° C. in vacuo with a $N_2$ purge. The white to off-white powder was obtained in 159.13 mg.

Example 10

Native Chemical Ligation: Protected Fragment 1-17 (SEQ ID NO: 13) to Protected Fragment 18-39 (SEQ ID NO: 14):

Preparation of reagents/substrates: 5 wt % solution of protected fragment 18-39 (SEQ ID NO: 14) (0.02 mmol, 103.275 mg, 1 equiv, 73.1 wt %) was weighed and dissolved in 1.96 mL of DMF. Similarly, 5 wt % solution of protected fragment 1-17 (SEQ ID NO: 13) (0.02 mmol, 65.68 mg, 1.0 equiv, 88.6 wt %) was weighed and dissolved in 1.24 mL of DMF. 10% (v/v) solution of DIEA (0.084 mmol, 14.32 µL, 4.2 equiv) of DIEA in DMF (128.88 uL) was prepared. 10 wt % solution of HATU (0.042 mmol, 2.0 equiv, 15.96 mg) was prepared in 143.64 uL acetonitrile.

Coupling and isolation: The protected fragment 18-39 (SEQ ID NO: 14) and protected fragment 1-17 (SEQ ID NO: 13) were mixed together, at 0° C. The DIEA and HATU solutions were added to the mixture at 0°. The reaction was stirred at 0° C. for 2 h. To it was added 2.0 mL of 17% NaCl/0.5% at 0° C., followed by addition of (2.2 mL) cold water at 0° C. and was stirred for an hour. The off-white precipitate was filtered and washed with water. It was dried under $N_2$ atmosphere in a vacuum oven at 40° C. overnight.

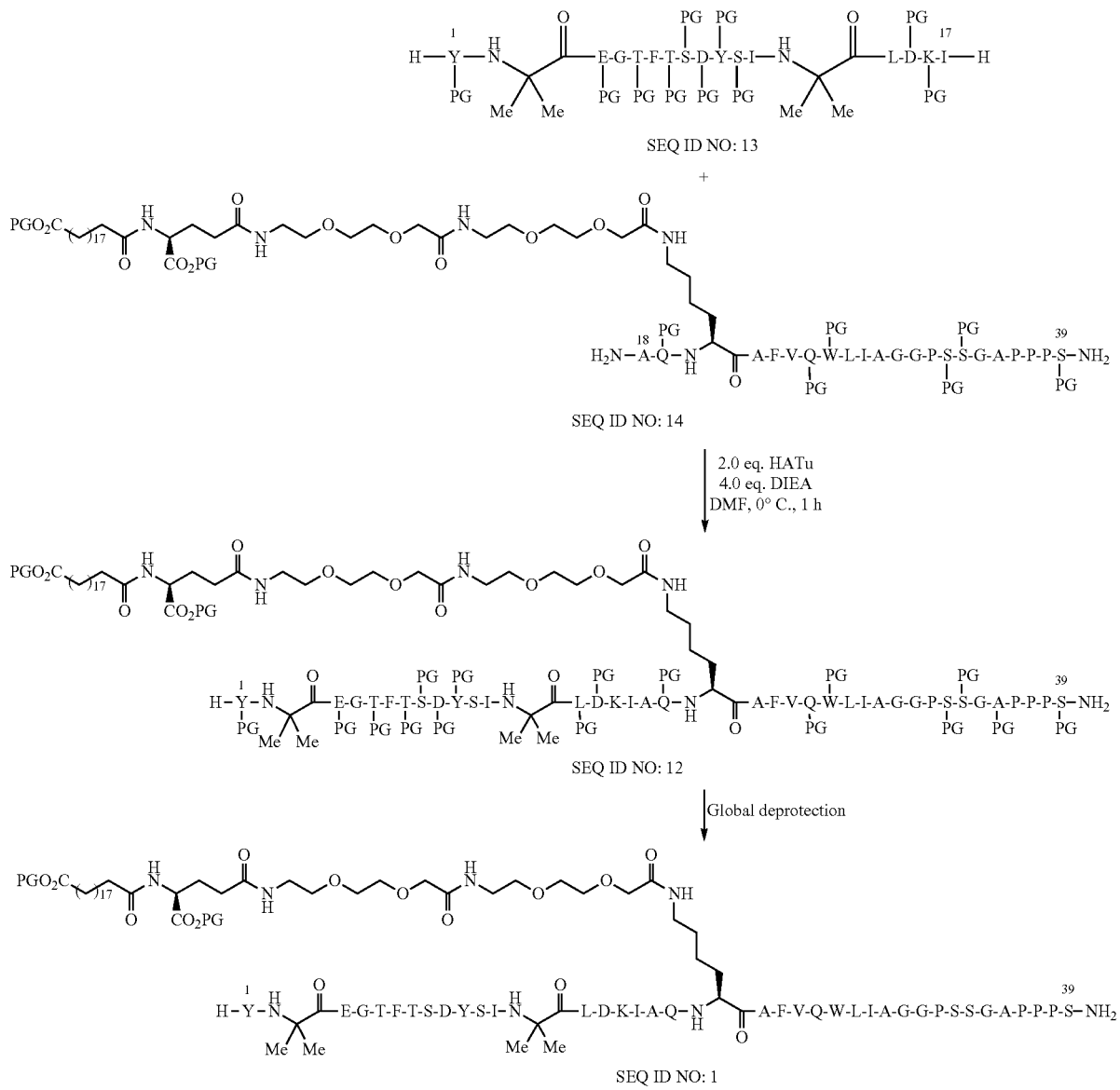

Global cleavage: The above isolated crude API was charged with DCM (1.5 mL/g; 315.75 uL), 20 volumes 92.25% TFA (3.87 mL), 2.5% DTT (0.105 mg), 2.5% water (0.105 mL), and 2.5% TIS (0.105 mL). It was stirred at room temperature for 2 h. It was poured into cold MTBE (30 mL) and kept at 2-4° C. for 30 minutes. It was then centrifuged at 3000 rpm for 3 minutes. The solid precipitate was washed with 2×30 mL MTBE and centrifuged each time. It was dried at 40° C. in vacuo with $N_2$ purge. The fully deprotected TZP (SEQ ID NO: 1) was obtained in 159.13 mg as an off-white powder.

Example 11

Native Chemical Ligation: Fragment 1-15 (SEQ ID NO: 15) to Fragment 16-39 (SEQ ID NO: 16):

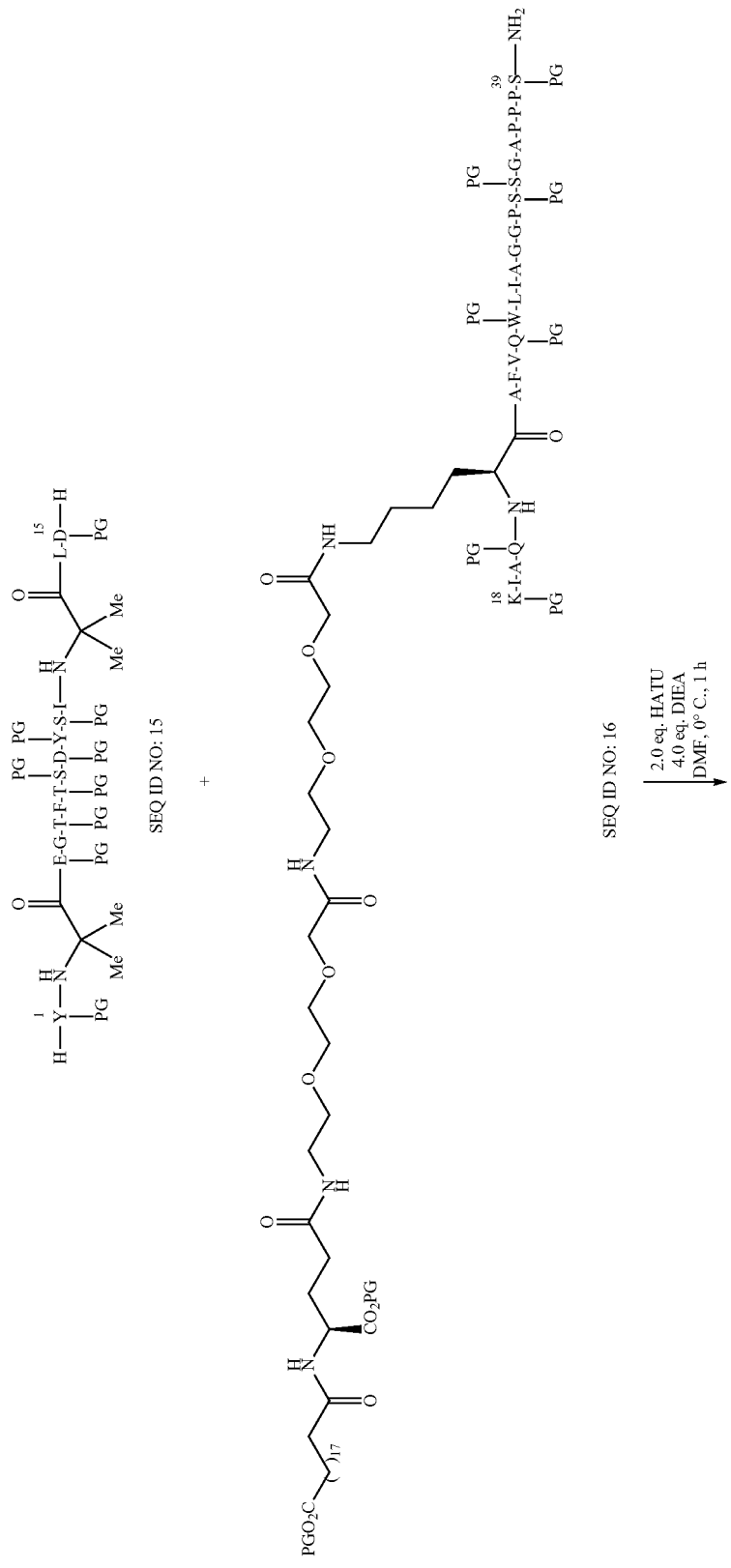

-continued
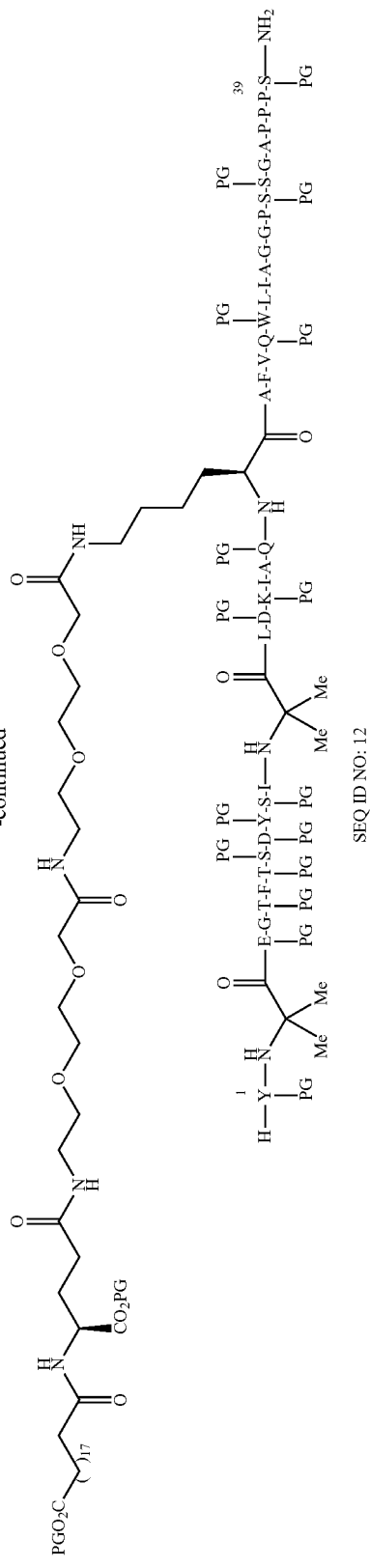
SEQ ID NO: 12
↓ Global deprotection
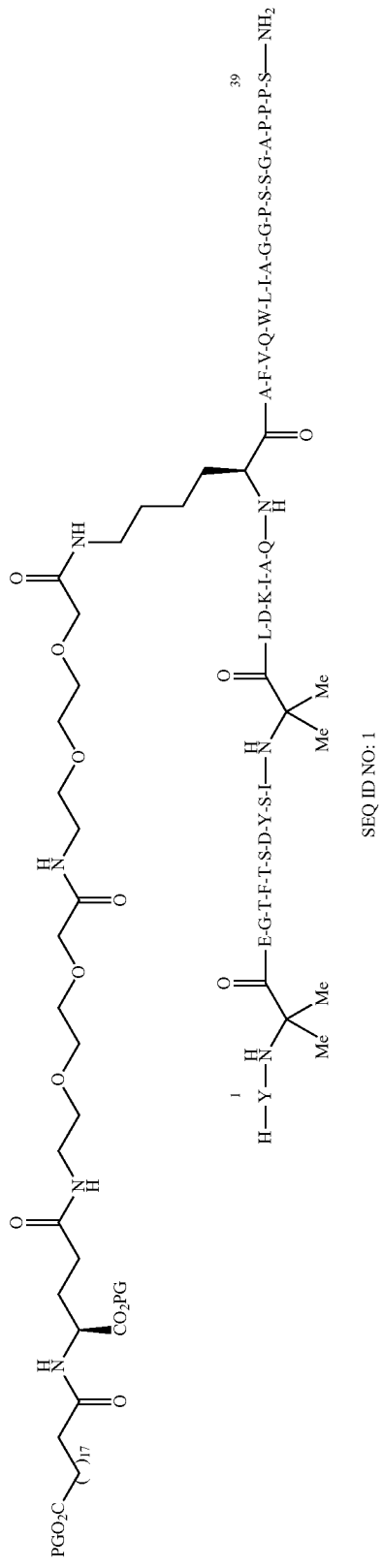
SEQ ID NO: 1

Preparation of reagents/substrates: A 5 wt % solution of protected fragment 16-39 (SEQ ID NO: 16) (0.02 mmol, 1 equiv, 113.606 mg, 72.31 wt %) was prepared in DMF (2158.5 uL). Similarly, a 5 wt % solution of protected fragment 1-15 (SEQ ID NO: 15) (0.026 mmol, 1.30 equiv, 66.95 mg, 88.76 wt %) was prepared in DMF (1272.05 uL). 10% (v/v) solution of DIEA (0.084 mmol, 4.2 equiv, 14.67 µL) was prepared in DMF (132 uL). 10 wt % solution of HATU (0.042 mmol, 2.1 equiv, 15.209 mg) was prepared in acetonitrile (143.64 uL).

Coupling and isolation: The protected fragment 16-39 (SEQ ID NO: 16) and protected fragment 1-15 (SEQ ID NO: 15) were mixed together, at 0° C. DIEA solution was charged to it at 0° C. followed the addition of HATU solution to the same. The reaction was stirred at 0° C. for 2 h. To it was added 2.0 mL of a 17% NaCl/0.5% at 0° C., followed by addition of cold water (2.2 mL) at 0° C. and was stirred for an hour. The off-white precipitate was filtered and washed with water. It was dried under $N_2$ atmosphere in a vacuum oven at 40° C. overnight.

Global cleavage: The above isolated crude API was charged with DCM (1.5 mL/g; 315.75 uL), 20 volumes 92.25% TFA (3.87 mL), 2.5% DTT (0.105 mg), 2.5% water (0.105 mL), and 2.5% TIS (0.105 mL). It was stirred at room temperature for 2 h. It was poured into cold MTBE (30 mL) and kept at 2-4° C. for 30 minutes. It was then centrifuged at 3000 rpm for 3 minutes. The solid precipitate was washed with 2×30 mL MTBE and centrifuged each time. It was dried at 40° C. in vacuo with a $N_2$ purge. The white to off-white powder was obtained in 159.13 mg.

Example 12: Amidation

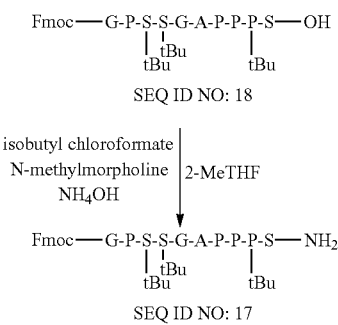

Fmoc-GPS(tBu)S(tBu)GAPPPS(tBu)-OH (SEQ ID NO: 18) (1.0625 g, 1 equiv.) was added to a reaction vessel under an inert atmosphere, and dissolved in 2-MeTHF (3.09 mL). The reaction vessel was placed in an ice bath and N-methylmorpholine (93.9 uL, 1 equiv.) was added to the solution. An additional 1 mL of 2-MeTHF was added. Isobutyl chloroformate (0.112 mL, 1 equiv.) was added to the reaction mixture and the mixture was allowed to stir for 10 minutes before the addition of ammonium hydroxide (0.14 mL, 4 equiv.). The resultant mixture was allowed to warm to room temperature and then mixed overnight (~18 hours). Equal parts EtOAc and water were then added to the reaction mixture. The aqueous layer was separated and the organic layer was concentrated under reduced pressure to afford a white solid, Fmoc-GPS(tBu)S(tBu)GAPPPS(tBu)-$NH_2$ (SEQ ID NO: 17). Mass found: 1242.6859 [M+H].

Example 13: Fmoc-Gly-Pro-Ser(tBu)-Ser(tBu)-Gly-OH (SEQ ID NO: 19)

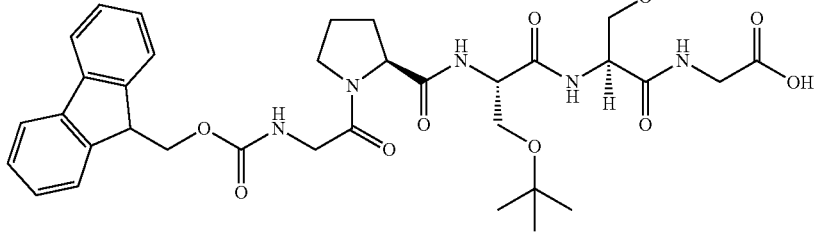

A crystallization screen was performed on Fmoc-G-P-S (tBu)-S(tBu)-G-OH (SEQ ID NO: 19) free form using various solvents and solvent mixtures. Different crystallization methods were employed including solvent-based techniques such as slurry, cooling, ambient and sub-ambient temperatures holding, solvent/anti-solvent addition, or combination of techniques, and non-solvent-based techniques such as heat stress.

Three solid forms were identified: Fmoc-G-P-S(tBu)-S(tBu)-G-OH (SEQ ID NO: 19) Form A, Fmoc-G-P-S(tBu)-S(tBu)-G-OH (SEQ ID NO: 19) Form C, and Fmoc-G-P-S(tBu)-S(tBu)-G-OH (SEQ ID NO: 19) Form D. Form A was a solvated form produced from 1-propanol (1-PrOH) or mixtures containing 1-PrOH (such as 1-PrOH/heptane). Form D is a solvated form produced from acetonitrile (ACN) or mixtures containing ACN (such as ACN/MTBE). Form C is a conversion product when Form D is isolated and dried.

Fmoc-G-P-S(tBu)-S(tBu)-G-OH (SEQ ID NO: 19)Form A Preparation 1:

Fmoc-G-P-S(tBu)-S(tBu)-G-OH (SEQ ID NO: 19) Form A was prepared in 1-propanol (1-PrOH). 16 mL 1-PrOH was added to 4.06 gram of amorphous solids of Fmoc-G-P-S(tBu)-S(tBu)-G-OH (SEQ ID NO: 19) and the sample was stirred at ambient conditions which yielded a red-orange solution. The solution was seeded with 2.8 mg of Fmoc-G-P-S(tBu)-S(tBu)-G-OH (SEQ ID NO: 19) Form A and then left at ambient conditions to continue stirring for 2 days. A light orange suspension was obtained, and solids were isolated by vacuum filtration using a 10 µm disposable filter, rinsed on the filter w/0.5 mL fresh 1-PrOH twice, and then collected and dried at 30° C. under vacuum for about 3-4 hours. The resulting white solids (3.2 gram) were consistent with Fmoc-G-P-S(tBu)-S(tBu)-G-OH (SEQ ID NO: 19) Form A.

Preparation 2:

Fmoc-G-P-S(tBu)-S(tBu)-G-OH (SEQ ID NO: 19) Form A was prepared in 1-propanol (1-PrOH) and heptane. Approximately 50 mg of amorphous Fmoc-G-P-S(tBu)-S(tBu)-G-OH (SEQ ID NO: 19) was dissolved in 0.6 mL 1-PrOH to form a clear yellow solution. The solution, in 30 μL aliquots, was added into 0.6 mL heptane yielding a clear light yellow solution. With stirring, additional 0.6 mL heptane was added to the solution and the sample was capped and stirred at ambient conditions for 2 days. A suspension was obtained, and solids were consistent with Fmoc-G-P-S(tBu)-S(tBu)-G-OH (SEQ ID NO: 19) Form A.

Preparation 3:

Fmoc-G-P-S(tBu)-S(tBu)-G-OH (SEQ ID NO: 19) Form A was prepared in 1-propanol (1-PrOH). Approximately 10 mg of amorphous Fmoc-G-P-S(tBu)-S(tBu)-G-OH (SEQ ID NO: 19) was dissolved in 0.1 mL 1-PrOH to form a clear yellow solution. The solution was stored at ambient conditions in capped vial for 1 day, then moved to freezer for 3 days. Solids observed in solution were consistent with Fmoc-G-P-S(tBu)-S(tBu)-G-OH SEQ ID NO: 19) Form A.

XRPD of Fmoc-G-P-S(tBu)-S(tBu)-G-OH (SEQ ID NO: 19) Form A

The XRPD pattern of crystalline Fmoc-G-P-S(tBu)-S(tBu)-G-OH (SEQ ID NO: 19) Form A was obtained on a Bruker D8 Endeavor X-ray powder diffractometer, equipped with a CuKα (1.5418A) source and a Linxeye detector, operating at 40 kV and 40 mA. The sample was scanned between 4 and 42 2θ°, with a step size of 0.009 2θ° and a scan rate of 0.5 seconds/step, and using 0.3° primary slit opening, and 3.9° PSD opening. The powder was packed on a quartz sample holder and a smooth surface as obtained using a glass slide. The diffraction patterns were collected at ambient temperature and relative humidity. Crystal peak positions were determined in MDI-Jade v7.9.9.

A prepared sample of Fmoc-G-P-S(tBu)-S(tBu)-G-OH (SEQ ID NO: 19) Form A was characterized by an XRPD pattern using CuKα radiation as having diffraction peaks (2-theta values) as described in Table 1 below, including a peak at 6.1° 2-Theta in combination with one or more of the peaks selected from 8.5, 11.7, 12.3, and 16.9° 2-Theta; with a tolerance for the diffraction angles of 0.2 degrees. A representative XRPD pattern of Fmoc-G-P-S(tBu)-S(tBu)-G-OH (SEQ ID NO: 19) Form A is shown in FIG. 1A.

TABLE 1

| | X-ray powder diffraction peaks of Fmoc—G—P—S(tBu)—S(tBu)—G—OH (SEQ ID NO: 19) Form A | |
|---|---|---|
| Peak | Angle (°2-Theta) +/− 0.2° | Relative Intensity (% of most intense peak) |
| 1 | 5.8 | 12.7% |
| 2 | 6.1 | 100.0% |
| 3 | 8.5 | 63.8% |
| 4 | 11.7 | 6.9% |
| 5 | 12.3 | 10.2% |
| 6 | 13.3 | 7.8% |
| 7 | 13.5 | 10.5% |
| 8 | 16.9 | 15.5% |
| 9 | 18.0 | 7.4% |
| 10 | 18.5 | 28.6% |
| 11 | 18.8 | 20.9% |
| 12 | 19.3 | 23.3% |
| 13 | 19.5 | 8.2% |
| 14 | 19.8 | 7.3% |
| 15 | 20.9 | 11.0% |
| 16 | 21.7 | 6.5% |
| 17 | 22.1 | 6.3% |
| 18 | 23.0 | 9.9% |

Fmoc-G-P-S(tBu)-S(tBu)-G-OH (SEQ ID NO: 19) Form C

Preparation 1:

0.5 mL ACN was added to 66.9 milligram of Fmoc-G-P-S(tBu)-S(tBu)-G-OH (SEQ ID NO: 19) Form A and the sample was stirred at 51° C. which yielded a clear colorless solution. The solution was moved to ambient conditions and small amounts of Fmoc-G-P-S(tBu)-S(tBu)-G-OH (SEQ ID NO: 19) Form A solids were added into the sample. The resulting thin suspension was stirred at ambient conditions for 3 days. A white suspension was obtained, and solids were isolated using a 0.45 μm nylon syringe filter and centrifuged at ambient conditions for 5 minutes. White solids on the filter were left at ambient conditions for air drying under gently N₂ flow for about 20 minutes. The resulting white solids are consistent with Fmoc-G-P-S(tBu)-S(tBu)-G-OH (SEQ ID NO: 19) Form C.

Preparation 2:

8 mL of 2:1 v/v ACN/MTBE was added to 2.25 gram of Fmoc-G-P-S(tBu)-S(tBu)-G-OH (SEQ ID NO: 19) Form A and the sample was stirred at ambient conditions yielding a white suspension. The suspension was seeded with Fmoc-G-P-S(tBu)-S(tBu)-G-OH (SEQ ID NO: 19) Form C and then left at ambient conditions to continue stirring for 2 days. Solids were isolated by vacuum filtration using a 10 μm disposable filter, rinsed on the filter w/1 mL of fresh 2:1 v/v ACN/MTBE, collected and dried at 30° C. under vacuum. The dried white solids were consistent with Fmoc-G-P-S(tBu)-S(tBu)-G-OH Form C.

XRPD of Fmoc-G-P-S(tBu)-S(tBu)-G-OH (SEQ ID NO: 19) Form C

The XRPD pattern of crystalline Fmoc-G-P-S(tBu)-S(tBu)-G-OH (SEQ ID NO: 19) Form C was obtained using the same procedures as Fmoc-G-P-S(tBu)-S(tBu)-G-OH (SEQ ID NO: 19) Form A.

A prepared sample of the Fmoc-G-P-S(tBu)-S(tBu)-G-OH (SEQ ID NO: 19) Form C was characterized by an XRPD pattern using CuKα radiation as having diffraction peaks (2-theta values) as described in Table 2 below, including a peak at 6.7° 2-Theta in combination with one or more of the peaks selected from the group consisting of 8.7, 10.6, 14.1, and 15.8° 2-Theta; with a tolerance for the diffraction angles of 0.2 degrees. A representative XRPD pattern of Fmoc-G-P-S(tBu)-S(tBu)-G-OH (SEQ ID NO: 19) Form C is shown in FIG. 11B.

TABLE 2

| | X-ray powder diffraction peaks of Fmoc—G—P—S(tBu)—S(tBu)—G—OH (SEQ ID NO: 19) Form C | |
|---|---|---|
| Peak | Angle (°2-Theta) +/− 0.2° | Relative Intensity (% of most intense peak) |
| 1 | 5.4 | 11.1% |
| 2 | 6.7 | 100.0% |
| 3 | 7.3 | 7.9% |

TABLE 2-continued

X-ray powder diffraction peaks of
Fmoc—G—P—S(tBu)—S(tBu)—G—OH (SEQ ID NO: 19) Form C
Fmoc—G—P—S(tBu)—S(tBu)—G—OH (SEQ ID NO: 19) Form C

| Peak | Angle (°2-Theta) +/− 0.2° | Relative Intensity (% of most intense peak) |
|---|---|---|
| 4 | 8.7 | 31.9% |
| 5 | 10.6 | 10.8% |
| 6 | 12.8 | 7.7% |
| 7 | 13.5 | 6.9% |
| 8 | 13.8 | 8.0% |
| 9 | 14.1 | 19.9% |
| 10 | 15.8 | 20.9% |
| 11 | 17.2 | 15.6% |
| 12 | 17.4 | 13.4% |
| 13 | 17.6 | 11.8% |
| 14 | 17.9 | 9.6% |
| 15 | 18.4 | 28.9% |
| 16 | 18.7 | 9.2% |
| 17 | 19.5 | 9.8% |
| 18 | 20.4 | 28.8% |
| 19 | 21.3 | 11.0% |
| 20 | 22.6 | 9.3% |

Fmoc-G-P-S(tBu)-S(tBu)-G-OH (SEQ ID NO: 19) Form D Preparation 1:

1 mL of 1:1 v/v ACN/MTBE was added to 72.6 milligram of Fmoc-G-P-S(tBu)-S(tBu)-G-OH (SEQ ID NO: 19) Form A and the sample was stirred at ambient conditions which resulted in a white suspension. The suspension was seeded with Fmoc-G-P-S(tBu)-S(tBu)-G-OH (SEQ ID NO: 19) Form C and then left at ambient conditions to continue stirring for 2 days. The wet solids from the slurry were consistent with Fmoc-G-P-S(tBu)-S(tBu)-G-OH (SEQ ID NO: 19) Form D, which was physically not stable and converted to Fmoc-G-P-S(tBu)-S(tBu)-G-OH (SEQ ID NO: 19) Form C upon isolation/drying.

XRPD of Fmoc-G-P-S(tBu)-S(tBu)-G-OH (SEQ ID NO: 19) Form D

The XRPD pattern of crystalline Fmoc-G-P-S(tBu)-S(tBu)-G-OH (SEQ ID NO: 19) Form C was obtained using the same procedures as Fmoc-G-P-S(tBu)-S(tBu)-G-OH (SEQ ID NO: 19) Form A, but the Fmoc-G-P-S(tBu)-S(tBu)-G-OH (SEQ ID NO: 19) Form B sample was scanned between 4 and 25 2θ° with a scan rate of 0.1 seconds/step.

Figure 1C:
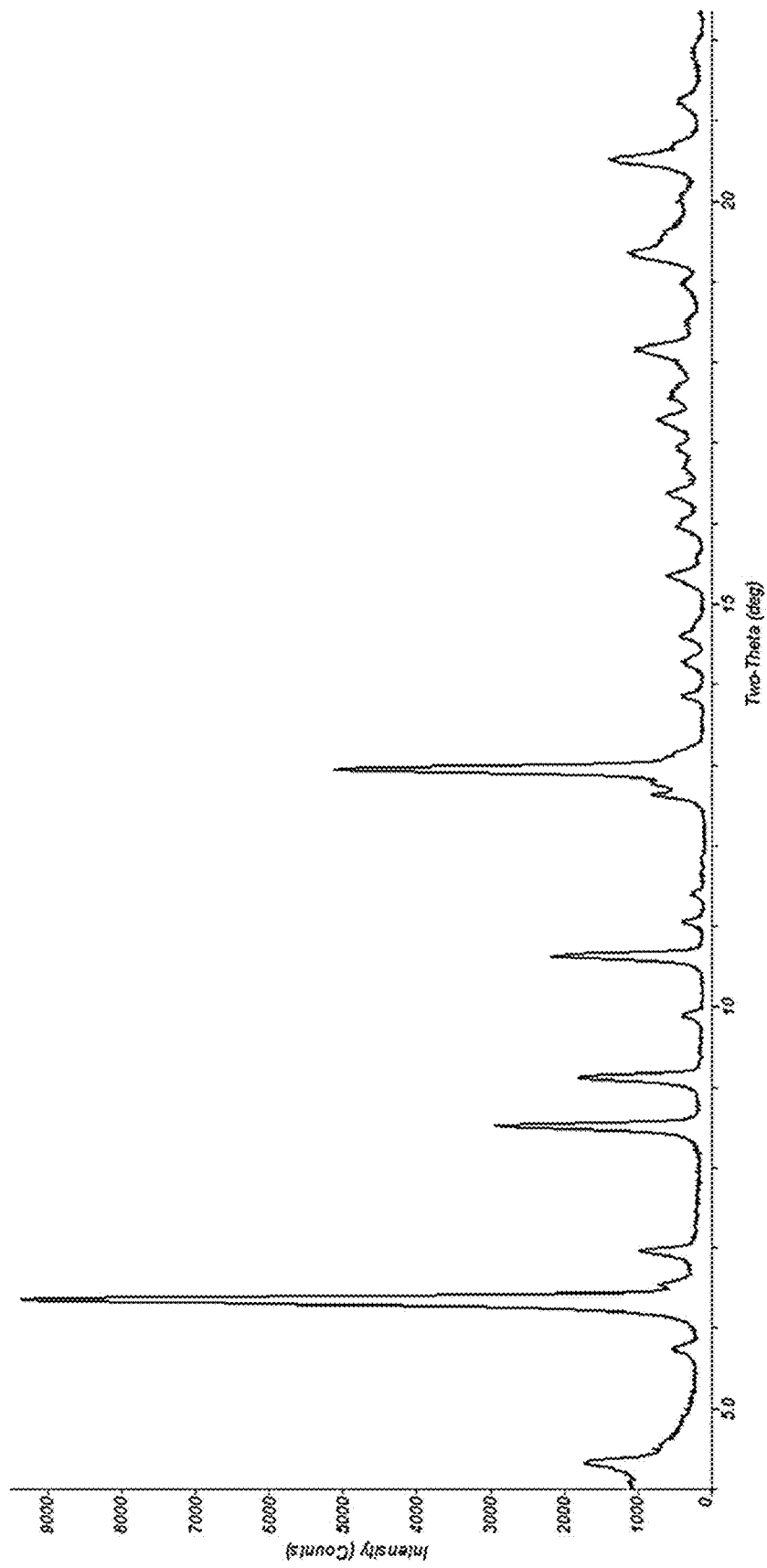

A prepared sample of the Fmoc-G-P-S(tBu)-S(tBu)-G-OH (SEQ ID NO: 19) Form D was characterized by an XRPD pattern using CuKα radiation as having diffraction peaks (2-theta values) as described in Table 3 below, including a peak at 6.1° 2-Theta, in combination with one or more of the peaks selected from the group consisting of 4.1, 10.4, and 12.7° 2-Theta; with a tolerance for the diffraction angles of 0.2 degrees. A representative XRPD pattern of Fmoc-G-P-S(tBu)-S(tBu)-G-OH (SEQ ID NO: 19) Form D is shown in FIG. 1C.

TABLE 3

X-ray powder diffraction peaks of
Fmoc—G—P—S(tBu)—S(tBu)—G—OH (SEQ ID NO: 19) Form D
Fmoc—G—P—S(tBu)—S(tBu)—G—OH (SEQ ID NO: 19) Form D

| Peak | Angle (°2-Theta) +/− 0.2° | Relative Intensity (% of most intense peak) |
|---|---|---|
| 1 | 4.1 | 9.2% |
| 2 | 6.1 | 100.0% |
| 3 | 6.7 | 8.7% |
| 4 | 8.3 | 30.2% |
| 5 | 8.9 | 18.2% |
| 6 | 10.4 | 22.5% |
| 7 | 12.7 | 55.1% |
| 8 | 15.1 | 5.2% |
| 9 | 17.9 | 9.4% |
| 10 | 19.1 | 9.3% |
| 11 | 20.3 | 12.6% |

Example 14: Gelation Studies

The gelling characteristics of peptide fragments was investigated under varying conditions, including: varying process solvents (DMSO/ACN and DMF), peptide fragment concentrations, gelation over time, processing shear rate (by modifying crossflow velocity), temperature conditions, and gelation reversibility.

Process Solvents

Figure 2A:
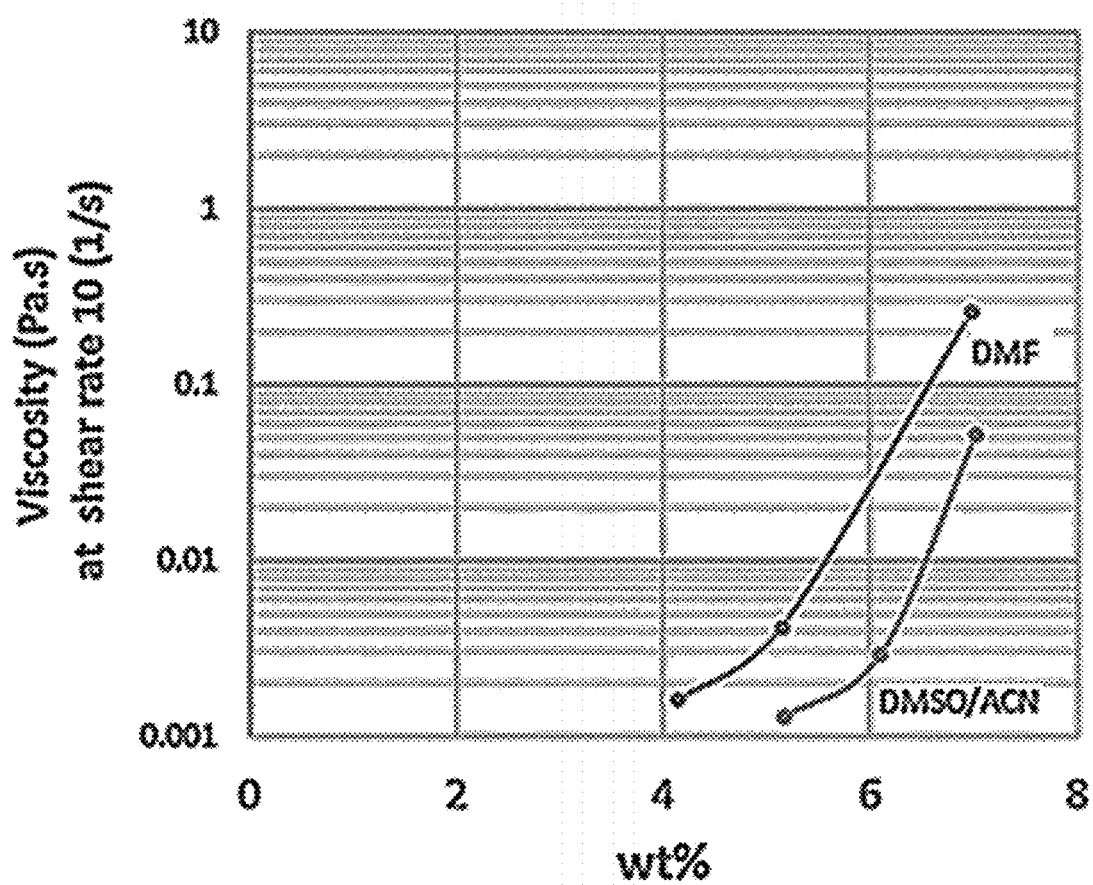
FIG. 2A, FIG. 2B, FIG. 2C, and FIG. 2D show viscosity measurements for peptide fragment gelation studies of the present disclosure.

Gelling characteristics of peptide fragments were investigated for DMSO/ACN and DMF at varying peptide fragment concentrations. Viscosity measurements (Pa·s) at a shear rate of 1/s are shown in FIG. 2A. Results showed that peptide product in DMF starts to get more viscous at lower concentration values when compared to DMSO/CAN.

Concentration and Time

Figure 2B:
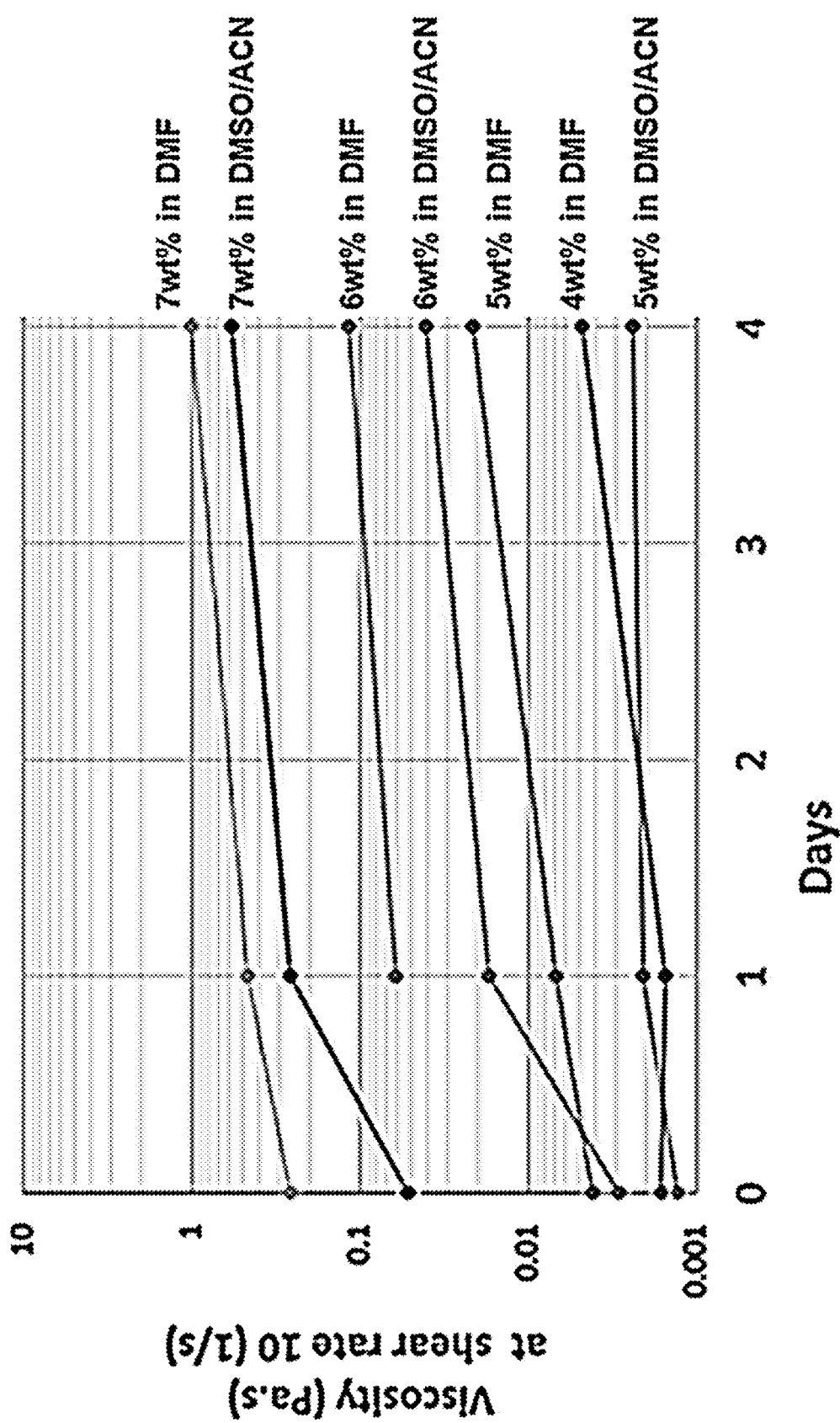

Gelling characteristics of peptide fragments were investigated for DMSO/ACN and DMF at varying peptide fragment concentrations over 4 days. Viscosity measurements (Pa·s) at a shear rate of 1/s are shown in FIG. 2B. Results showed that viscosity of the formulation increased with peptide fragment concentrations, and increased over time, in both solvent systems.

Shear Rate

Figure 2C:
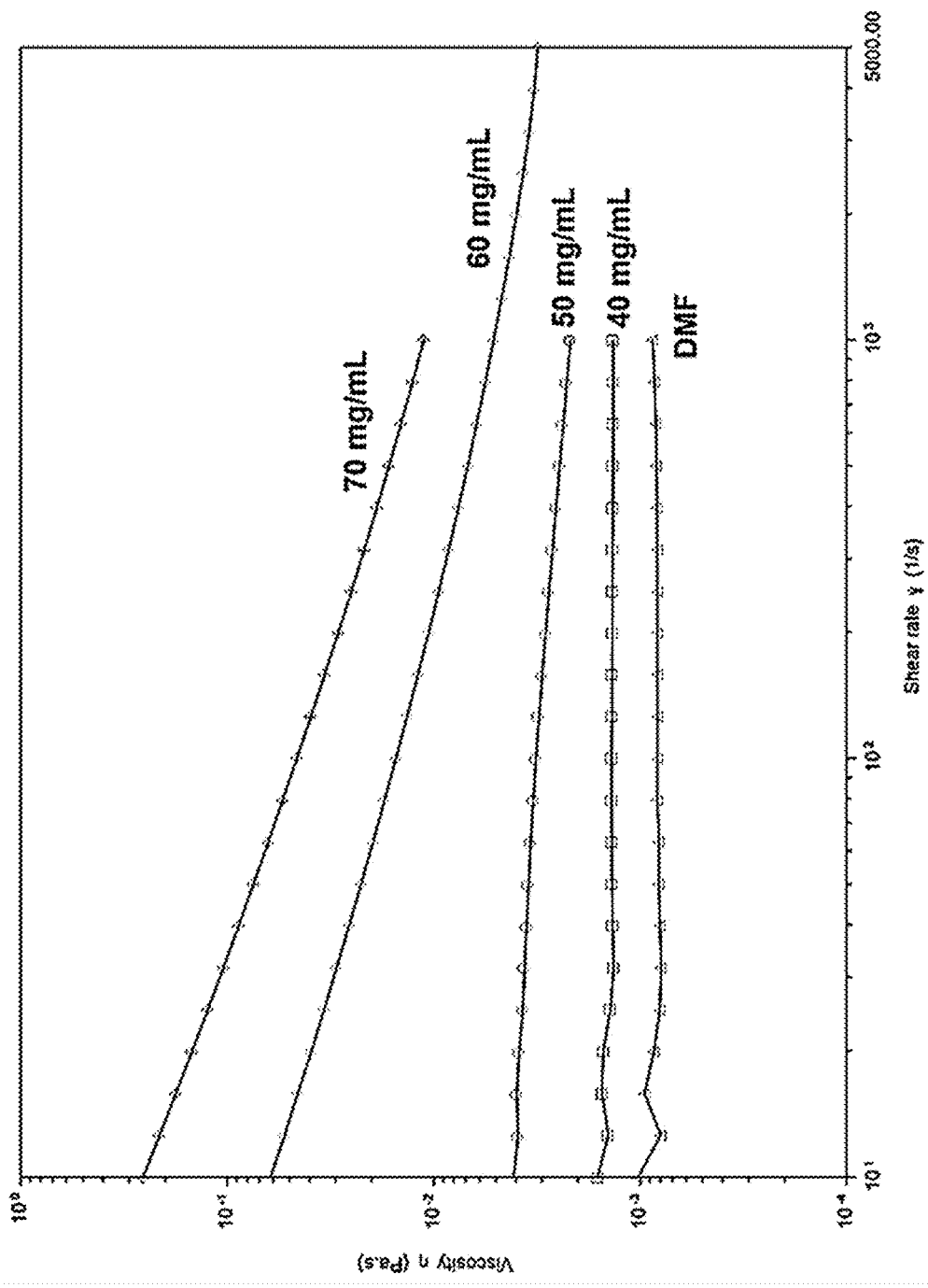

Gelling characteristics of peptide fragments were investigated for peptide fragment concentrations in DMF of 40 mg/mL, 50 mg/mL, 60 mg/mL, and 70 mg/mL at varying shear rate conditions. Viscosity measurements (Pa·s are shown in FIG. 2C. Results showed that 40 mg/mL and 50 mg/mL concentrations of peptide fragments in DMF maintained a consistent viscosity as shear rate was increased, while 60 mg/mL and 70 mg/mL concentrations of peptide fragments in DMF had notable decreases in viscosity as shear rate was increased.

Figure 2D:
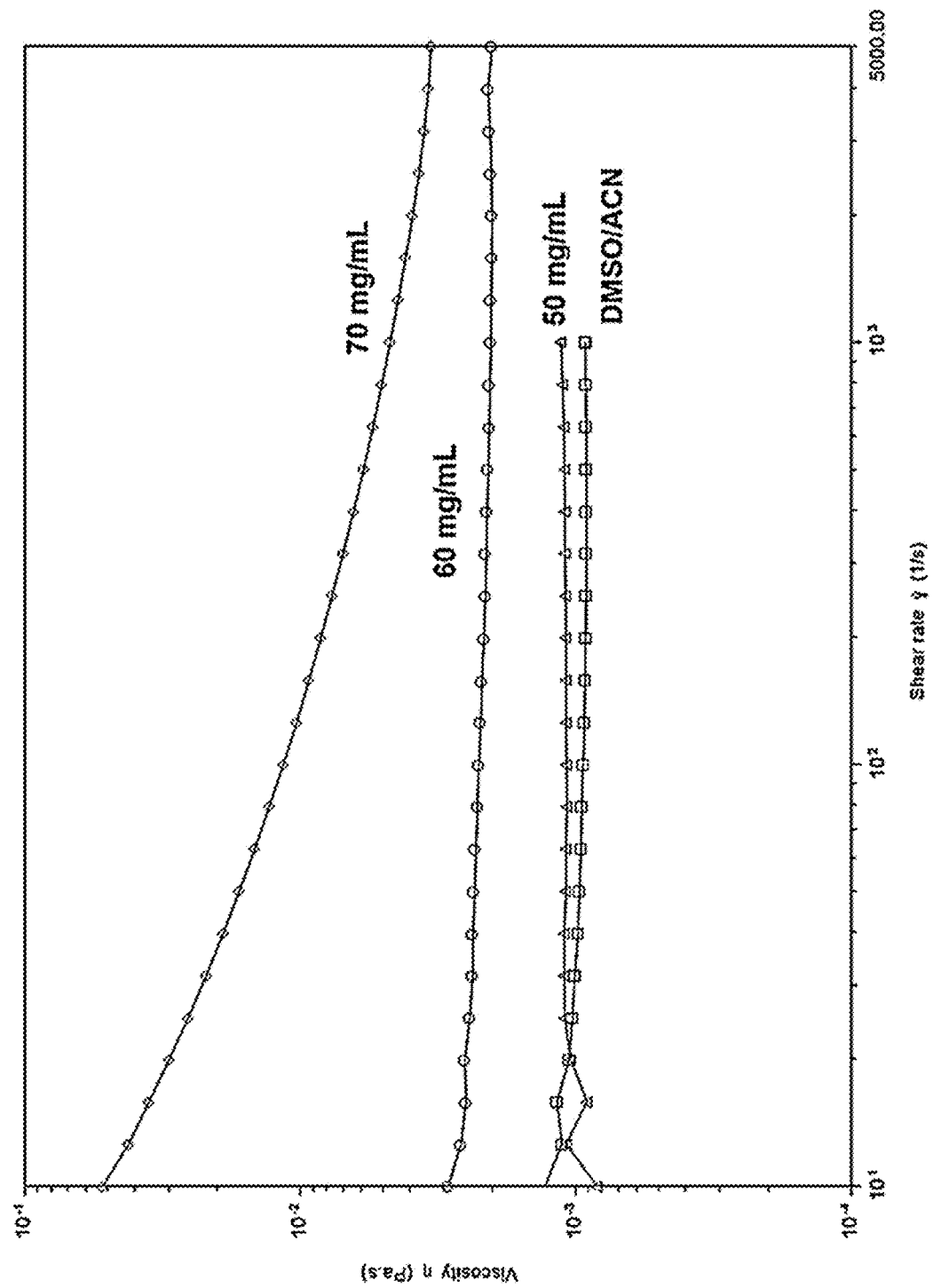

Gelling characteristics of peptide fragments were investigated for peptide fragment concentrations in DMSO/ACN of 50 mg/mL, 60 mg/mL, and 70 mg/mL at varying shear rate conditions. Viscosity measurements (Pa·s are shown in FIG. 2D. Results showed that 50 mg/mL and 60 mg/mL concentrations of peptide fragments in DMSO/ACN maintained a consistent viscosity as shear rate was increased, while 70 mg/mL concentrations of peptide fragments in DMSO/ACN had notable decreases in viscosity as shear rate was increased.

Parametric Ranges

Results from the gelation studies were used to study and define improved parametric conditions (temperature, concentration, shear rate, cross flow velocity) for the nanofiltration of peptide fragments of the present disclosure. Improved parametric conditions included: (i) temperature from 10 to 34° C. (target of about 20° C.), (ii) turbulent flow/crossflow velocity from 1.94 to 2.46 m/s (target of about 2.2 m/s); (iii) laminar flow/shear rate from $2.1 \times 10^3$ to $2.7 \times 10^3$ 1/s (target of about $2.4 \times 10^3$ 1/s); (iv) primary concentration target from 32.8 to 47.2 mg/mL (target of about 40 mg/mL); and (v) secondary concentration target from 37 to 53 mg/mL (target of about 45 mg/mL).

High temperature, low peptide fragment concentration, high shear rate and high crossflow velocity may be leveraged to reduce viscosity and consequently reverse gelation.

SEQ ID NO: 1

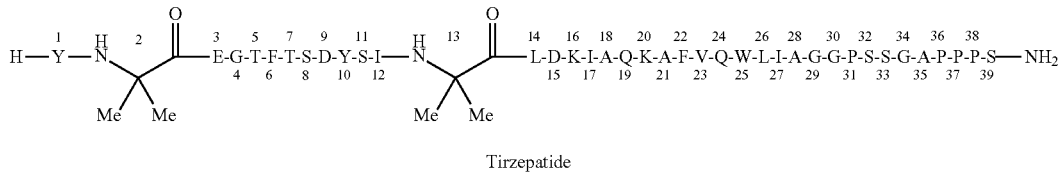

Tirzepatide 20 wherein K at position 20 is chemically modified through conjugation to the epsilon-amino group of the K side-chain with (2-[2-(2-Amino-ethoxy)-ethoxy]-acetyl)$_2$-(γGlu)$_1$-CO—(CH$_2$)$_{18}$—CO$_2$H.

SEQ ID NO: 2 - Hydrazide Fragment 1-17

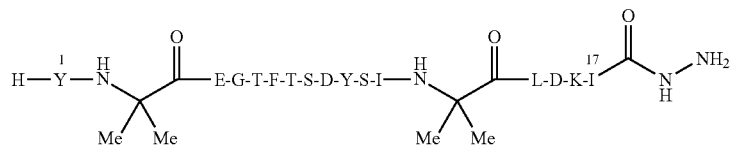

SEQ ID NO: 3 - Cysteine-18 Fragment 18-39

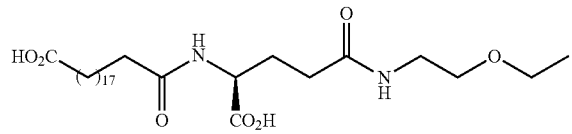

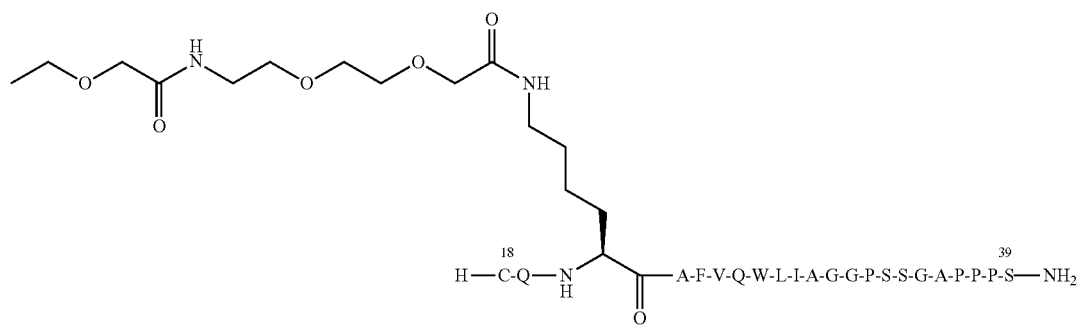

SEQ ID NO: 4 - Thioester fragment 1-17

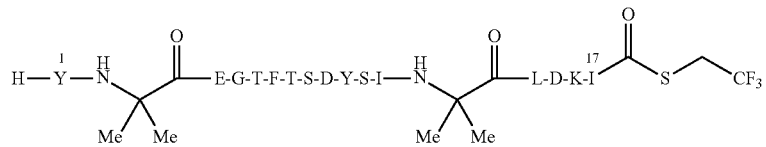

SEQ ID NO: 5 - TZP cysteine-18 analogue

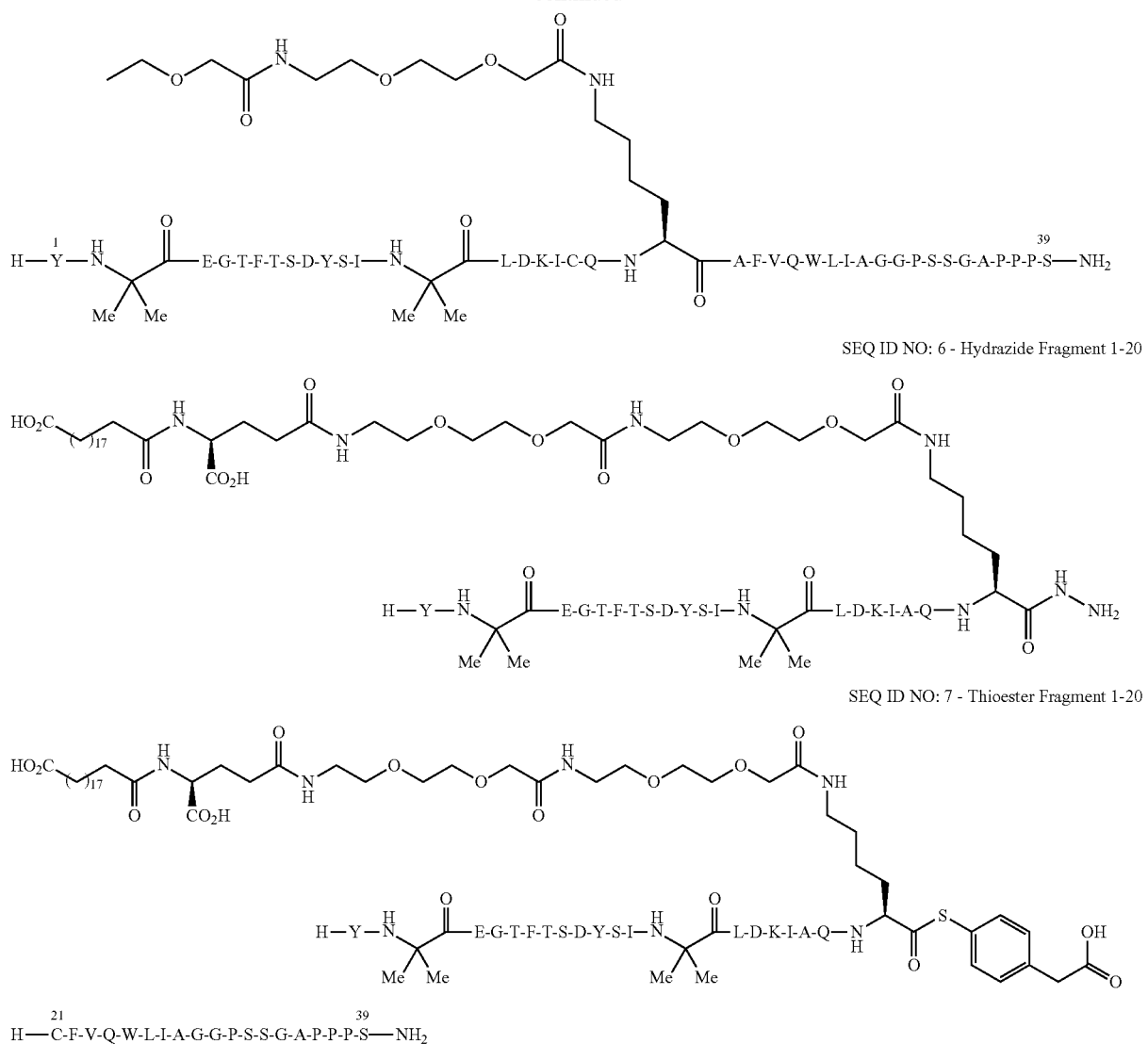
SEQ ID NO: 6 - Hydrazide Fragment 1-20
SEQ ID NO: 7 - Thioester Fragment 1-20
SEQ ID NO: 9 - TZP cysteine-21 analogue
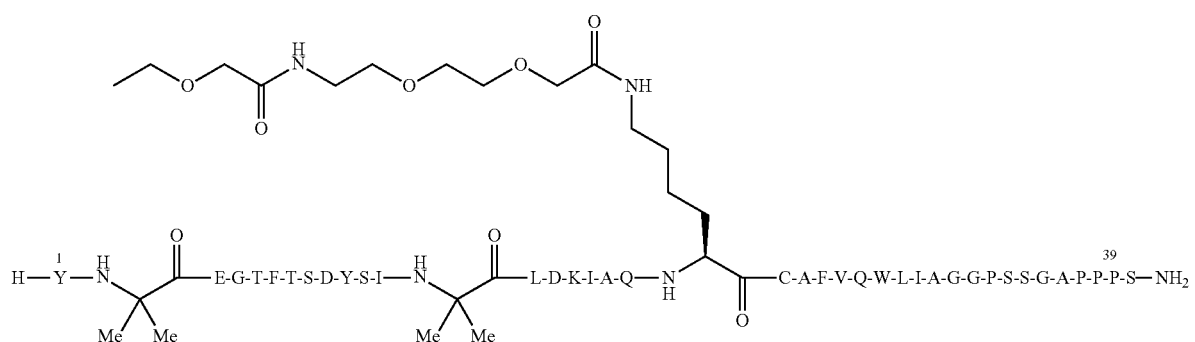

SEQ ID NO: 10 - Protected Fragment 1-21
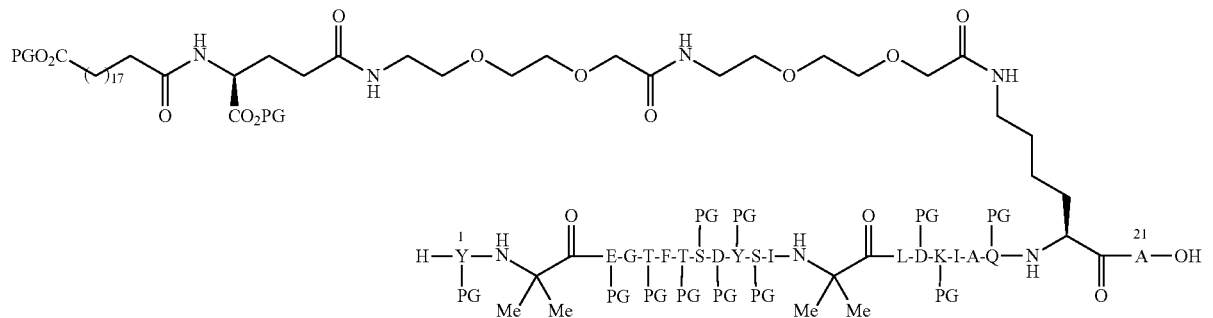
SEQ ID NO: 11 - Protected Fragment 22-39
SEQ ID NO: 12 - Protected TZP
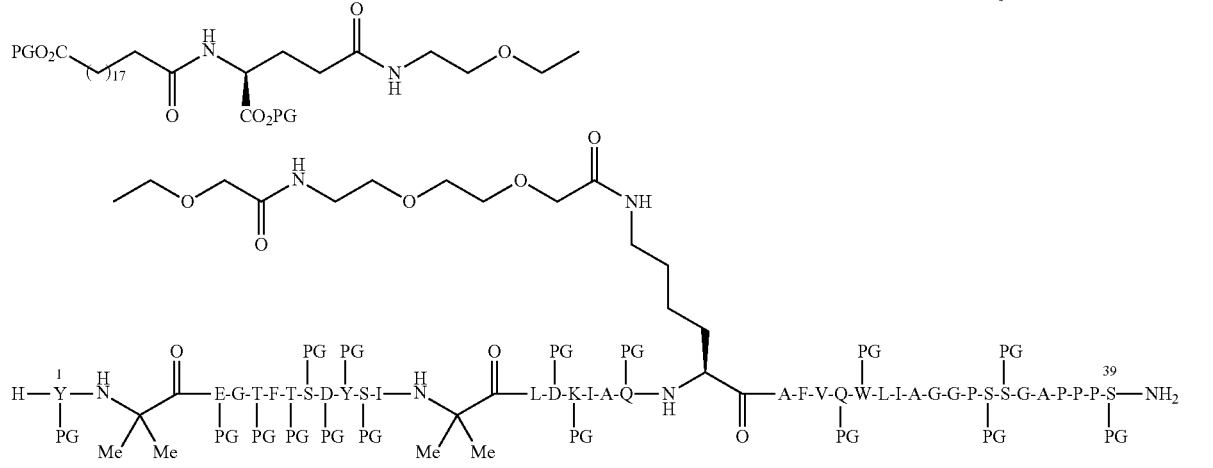
SEQ ID NO: - Protected Fragment 1-17
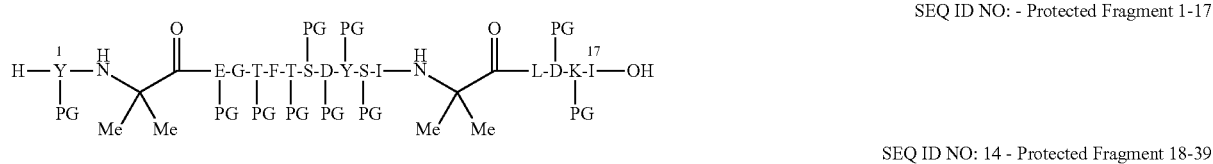
SEQ ID NO: 14 - Protected Fragment 18-39
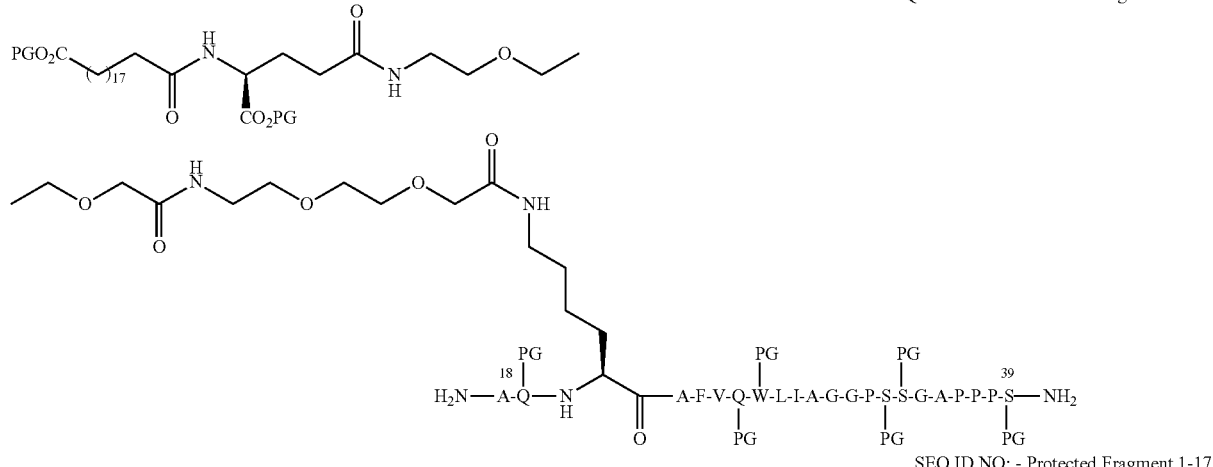
SEQ ID NO: - Protected Fragment 1-17
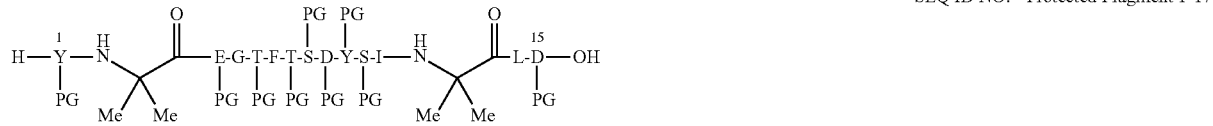

SEQ ID NO: 16 - Protected Fragment 16-39

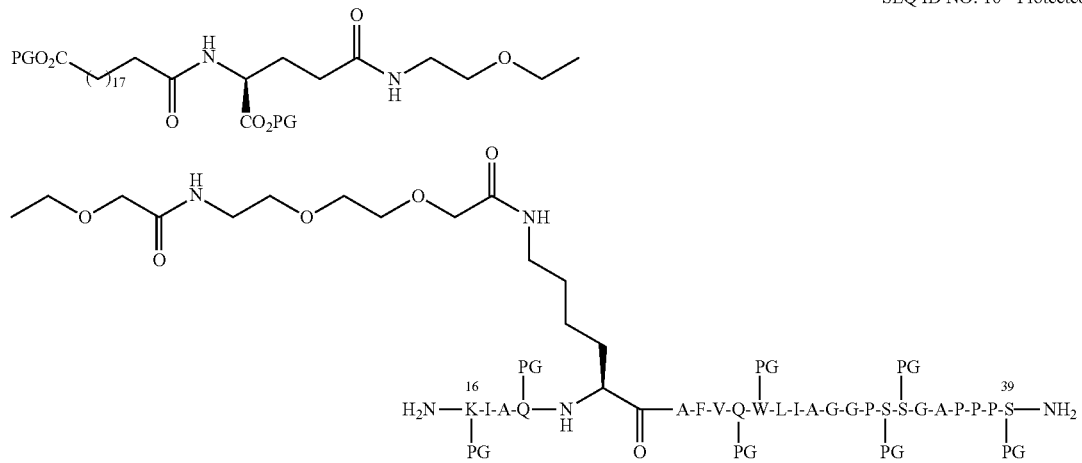

---

SEQUENCE LISTING

```
Sequence total quantity: 19
SEQ ID NO: 1            moltype = AA  length = 39
FEATURE                 Location/Qualifiers
source                  1..39
                        mol_type = protein
                        organism = synthetic construct
SITE                    2
                        note = X at position 2 is Aib
SITE                    13
                        note = X at position 13 is Aib
SITE                    20
                        note = K at position 20 is chemically modified through
                         conjugation to the epsilon-amino group of the K side-chain
                         with
                         (2-[2-(2-Amino-ethoxy)-ethoxy]-acetyl)2-(gamma-Glu)-CO-(CH2
                         )18-CO2H
SITE                    39
                        note = The C-terminal amino acid is amidated as a
                         C-terminal primary amide
SEQUENCE: 1
YXEGTFTSDY SIXLDKIAQK AFVQWLIAGG PSSGAPPPS                                    39

SEQ ID NO: 2            moltype = AA  length = 17
FEATURE                 Location/Qualifiers
source                  1..17
                        mol_type = protein
                        organism = synthetic construct
SITE                    2
                        note = X at position 2 is Aib
SITE                    13
                        note = X at position 13 is Aib
SITE                    17
                        note = The C-terminal amino acid includes a C-terminal
                         hydrazide
SEQUENCE: 2
YXEGTFTSDY SIXLDKI                                                           17

SEQ ID NO: 3            moltype = AA  length = 22
FEATURE                 Location/Qualifiers
source                  1..22
                        mol_type = protein
                        organism = synthetic construct
SITE                    3
                        note = K at position 20 is chemically modified through
                         conjugation to the epsilon-amino group of the K side-chain
                         with
                         (2-[2-(2-Amino-ethoxy)-ethoxy]-acetyl)2-(gamma-Glu)-CO-(CH2
                         )18-CO2H
SITE                    22
                        note = The C-terminal amino acid is amidated as a
                         C-terminal primary amide
```

```
SEQUENCE: 3
CQKAFVQWLI AGGPSSGAPP PS                                          22

SEQ ID NO: 4            moltype = AA  length = 17
FEATURE                 Location/Qualifiers
source                  1..17
                        mol_type = protein
                        organism = synthetic construct
SITE                    2
                        note = X at position 2 is Aib
SITE                    13
                        note = X at position 13 is Aib
SITE                    17
                        note = The C-terminal amino acid includes a C-terminal
                        2,2,2-trifluoroethanethiol
SEQUENCE: 4
YXEGTFTSDY SIXLDKI                                                17

SEQ ID NO: 5            moltype = AA  length = 39
FEATURE                 Location/Qualifiers
source                  1..39
                        mol_type = protein
                        organism = synthetic construct
SITE                    2
                        note = X at position 2 is Aib
SITE                    13
                        note = X at position 13 is Aib
SITE                    20
                        note = K at position 20 is chemically modified through
                         conjugation to the epsilon-amino group of the K side-chain
                         with
                         (2-[2-(2-Amino-ethoxy)-ethoxy]-acetyl)2-(gamma-Glu)-CO-(CH2
                         )18-CO2H
SITE                    39
                        note = The C-terminal amino acid is amidated as a
                         C-terminal primary amide
SEQUENCE: 5
YXEGTFTSDY SIXLDKICQK AFVQWLIAGG PSSGAPPPS                         39

SEQ ID NO: 6            moltype = AA  length = 20
FEATURE                 Location/Qualifiers
source                  1..20
                        mol_type = protein
                        organism = synthetic construct
SITE                    2
                        note = X at position 2 is Aib
SITE                    13
                        note = X at position 13 is Aib
SITE                    20
                        note = K at position 20 is chemically modified through
                         conjugation to the epsilon-amino group of the K side-chain
                         with
                         (2-[2-(2-Amino-ethoxy)-ethoxy]-acetyl)2-(gamma-Glu)-CO-(CH2
                         )18-CO2H
SITE                    20
                        note = The C-terminal amino acid includes a C-terminal
                         hydrazide
SEQUENCE: 6
YXEGTFTSDY SIXLDKIAQK                                             20

SEQ ID NO: 7            moltype = AA  length = 20
FEATURE                 Location/Qualifiers
source                  1..20
                        mol_type = protein
                        organism = synthetic construct
SITE                    2
                        note = X at position 2 is Aib
SITE                    13
                        note = X at position 13 is Aib
SITE                    20
                        note = K at position 20 is chemically modified through
                         conjugation to the epsilon-amino group of the K side-chain
                         with
                         (2-[2-(2-Amino-ethoxy)-ethoxy]-acetyl)2-(gamma-Glu)-CO-(CH2
                         )18-CO2H
SITE                    20
                        note = The C-terminal amino acid includes a C-terminal
                         4-mercaptophenylacetic acid
SEQUENCE: 7
```

```
YXEGTFTSDY SIXLDKIAQK                                                      20

SEQ ID NO: 8              moltype = AA  length = 19
FEATURE                   Location/Qualifiers
source                    1..19
                          mol_type = protein
                          organism = synthetic construct
SITE                      19
                          note = The C-terminal amino acid is amidated as a
                          C-terminal primary amide
SEQUENCE: 8
CFVQWLIAGG PSSGAPPPS                                                       19

SEQ ID NO: 9              moltype = AA  length = 39
FEATURE                   Location/Qualifiers
source                    1..39
                          mol_type = protein
                          organism = synthetic construct
SITE                      2
                          note = X at position 2 is Aib
SITE                      13
                          note = X at position 13 is Aib
SITE                      20
                          note = K at position 20 is chemically modified through
                          conjugation to the epsilon-amino group of the K side-chain
                          with
                          (2-[2-(2-Amino-ethoxy)-ethoxy]-acetyl)2-(gamma-Glu)-CO-(CH2
                          )18-CO2H
SITE                      39
                          note = The C-terminal amino acid is amidated as a
                          C-terminal primary amide
SEQUENCE: 9
YXEGTFTSDY SIXLDKIAQK CFVQWLIAGG PSSGAPPPS                                  39

SEQ ID NO: 10             moltype = AA  length = 21
FEATURE                   Location/Qualifiers
source                    1..21
                          mol_type = protein
                          organism = synthetic construct
SITE                      2
                          note = X at position 2 is Aib
SITE                      13
                          note = X at position 13 is Aib
SITE                      20
                          note = K at position 20 is chemically modified through
                          conjugation to the epsilon-amino group of the K side-chain
                          with
                          (2-[2-(2-Amino-ethoxy)-ethoxy]-acetyl)2-(gamma-Glu)-CO-(CH2
                          )18-CO2H having carboxyl protecting groups
VARIANT                   1
                          note = Y at position 1 is chemically modified with a
                          protecting group, such as a Fluorenylmethoxycarbonyl
                          protecting group (Fmoc), tert-butyloxycarbonyl protecting
                          group (Boc), or triphenylmethyl protecting group
VARIANT                   3
                          note = E at position 3 is chemically modified with a
                          protecting group, such as a Fluorenylmethoxycarbonyl
                          protecting group (Fmoc), tert-butyloxycarbonyl protecting
                          group (Boc), or triphenylmethyl protecting group
VARIANT                   5
                          note = T at position 5 is chemically modified with a
                          protecting group, such as a Fluorenylmethoxycarbonyl
                          protecting group (Fmoc), tert-butyloxycarbonyl protecting
                          group (Boc), or triphenylmethyl protecting group
VARIANT                   7
                          note = T at position 7 is chemically modified with a
                          protecting group, such as a Fluorenylmethoxycarbonyl
                          protecting group (Fmoc), tert-butyloxycarbonyl protecting
                          group (Boc), or triphenylmethyl protecting group
VARIANT                   8
                          note = S at position 8 is chemically modified with a
                          protecting group, such as a Fluorenylmethoxycarbonyl
                          protecting group (Fmoc), tert-butyloxycarbonyl protecting
                          group (Boc), or triphenylmethyl protecting group
VARIANT                   9
                          note = D at position 9 is chemically modified with a
                          protecting group, such as a Fluorenylmethoxycarbonyl
                          protecting group (Fmoc), tert-butyloxycarbonyl protecting
                          group (Boc), or triphenylmethyl protecting group
```

| | |
|---|---|
| VARIANT | 10<br>note = Y at position 10 is chemically modified with a protecting group, such as a Fluorenylmethoxycarbonyl protecting group (Fmoc), tert-butyloxycarbonyl protecting group (Boc), or triphenylmethyl protecting group |
| VARIANT | 11<br>note = S at position 11 is chemically modified with a protecting group, such as a Fluorenylmethoxycarbonyl protecting group (Fmoc), tert-butyloxycarbonyl protecting group (Boc), or triphenylmethyl protecting group |
| VARIANT | 15<br>note = D at position 15 is chemically modified with a protecting group, such as a Fluorenylmethoxycarbonyl protecting group (Fmoc), tert-butyloxycarbonyl protecting group (Boc), or triphenylmethyl protecting group |
| VARIANT | 16<br>note = K at position 16 is chemically modified with a protecting group, such as a Fluorenylmethoxycarbonyl protecting group (Fmoc), tert-butyloxycarbonyl protecting group (Boc), or triphenylmethyl protecting group |
| VARIANT | 19<br>note = Q at position 19 is chemically modified with a protecting group, such as a Fluorenylmethoxycarbonyl protecting group (Fmoc), tert-butyloxycarbonyl protecting group (Boc), or triphenylmethyl protecting group |
| SITE | 21<br>note = The C-terminal amino acid is amidated as a C-terminal primary amide |
| SEQUENCE: 10 | |
| YXEGTFTSDY SIXLDKIAQK A | 21 |
| | |
| SEQ ID NO: 11 | moltype = AA  length = 18 |
| FEATURE | Location/Qualifiers |
| source | 1..18<br>mol_type = protein<br>organism = synthetic construct |
| SITE | 18<br>note = The C-terminal amino acid is amidated as a C-terminal primary amide |
| VARIANT | 3<br>note = Q at position 3 is chemically modified with a protecting group, such as a Fluorenylmethoxycarbonyl protecting group (Fmoc), tert-butyloxycarbonyl protecting group (Boc), or triphenylmethyl protecting group |
| VARIANT | 4<br>note = W at position 4 is chemically modified with a protecting group, such as a Fluorenylmethoxycarbonyl protecting group (Fmoc), tert-butyloxycarbonyl protecting group (Boc), or triphenylmethyl protecting group |
| VARIANT | 11<br>note = S at position 11 is chemically modified with a protecting group, such as a Fluorenylmethoxycarbonyl protecting group (Fmoc), tert-butyloxycarbonyl protecting group (Boc), or triphenylmethyl protecting group |
| VARIANT | 12<br>note = S at position 12 is chemically modified with a protecting group, such as a Fluorenylmethoxycarbonyl protecting group (Fmoc), tert-butyloxycarbonyl protecting group (Boc), or triphenylmethyl protecting group |
| VARIANT | 18<br>note = S at position 18 is chemically modified with a protecting group, such as a Fluorenylmethoxycarbonyl protecting group (Fmoc), tert-butyloxycarbonyl protecting group (Boc), or triphenylmethyl protecting group |
| SEQUENCE: 11 | |
| FVQWLIAGGP SSGAPPPS | 18 |
| | |
| SEQ ID NO: 12 | moltype = AA  length = 39 |
| FEATURE | Location/Qualifiers |
| source | 1..39<br>mol_type = protein<br>organism = synthetic construct |
| SITE | 2<br>note = X at position 2 is Aib |
| SITE | 13<br>note = X at position 13 is Aib |
| SITE | 20<br>note = K at position 20 is chemically modified through conjugation to the epsilon-amino group of the K side-chain |

-continued

```
                       with
                       (2-[2-(2-Amino-ethoxy)-ethoxy]-acetyl)2-(gamma-Glu)-CO-(CH2
                       )18-CO2H having carboxyl protecting groups
VARIANT                1
                       note = Y at position 1 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                3
                       note = E at position 3 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                5
                       note = T at position 5 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                7
                       note = T at position 7 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                8
                       note = S at position 8 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                9
                       note = D at position 9 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                10
                       note = Y at position 10 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                11
                       note = S at position 11 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                15
                       note = D at position 15 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                16
                       note = K at position 16 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                19
                       note = Q at position 19 is chemically modified with a
                       protecting group, such as a Fluorenylmethoxycarbonyl
                       protecting group (Fmoc), tert-butyloxycarbonyl protecting
                       group (Boc), or triphenylmethyl protecting group
SITE                   39
                       note = The C-terminal amino acid is amidated as a
                       C-terminal primary amide
VARIANT                24
                       note = Q at position 24 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                25
                       note = W at position 25 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                32
                       note = S at position 32 is chemically modified with a
                       protecting group, such as a Fluorenylmethoxycarbonyl
                       protecting group (Fmoc), tert-butyloxycarbonyl protecting
                       group (Boc), or triphenylmethyl protecting group
VARIANT                33
                       note = S at position 33 is chemically modified with a
                       protecting group, such as a Fluorenylmethoxycarbonyl
```

-continued

```
                                protecting group (Fmoc), tert-butyloxycarbonyl protecting
                                group (Boc), or triphenylmethyl protecting group
VARIANT                         39
                                note = S at position 39 is chemically modified with a
                                protecting group, such as a Fluorenylmethoxycarbonyl
                                protecting group (Fmoc), tert-butyloxycarbonyl protecting
                                group (Boc), or triphenylmethyl protecting group
SEQUENCE: 12
YXEGTFTSDY SIXLDKIAQK AFVQWLIAGG PSSGAPPPS                                          39

SEQ ID NO: 13                   moltype = AA  length = 17
FEATURE                         Location/Qualifiers
source                          1..17
                                mol_type = protein
                                organism = synthetic construct
SITE                            2
                                note = X at position 2 is Aib
SITE                            13
                                note = X at position 13 is Aib
VARIANT                         1
                                note = Y at position 1 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         3
                                note = E at position 3 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         5
                                note = T at position 5 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         7
                                note = T at position 7 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         8
                                note = S at position 8 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         9
                                note = D at position 9 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         10
                                note = Y at position 10 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         11
                                note = S at position 11 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         15
                                note = D at position 15 is chemically modified with a
                                protecting group, such as a Fluorenylmethoxycarbonyl
                                protecting group (Fmoc), tert-butyloxycarbonyl protecting
                                group (Boc), or triphenylmethyl protecting group
VARIANT                         16
                                note = K at position 16 is chemically modified with a
                                protecting group, such as a Fluorenylmethoxycarbonyl
                                protecting group (Fmoc), tert-butyloxycarbonyl protecting
                                group (Boc), or triphenylmethyl protecting group
SITE                            17
                                note = The C-terminal amino acid is amidated as a
                                C-terminal primary amide
SEQUENCE: 13
YXEGTFTSDY SIXLDKI                                                                 17

SEQ ID NO: 14                   moltype = AA  length = 22
FEATURE                         Location/Qualifiers
source                          1..22
                                mol_type = protein
```

|  |  |
|---|---|
| SITE | organism = synthetic construct<br>3<br>note = K at position 3 is chemically modified through conjugation to the epsilon-amino group of the K side-chain with (2-[2-(2-Amino-ethoxy)-ethoxy]-acetyl)2-(gamma-Glu)-CO-(CH2)18-CO2H having carboxyl protecting groups |
| VARIANT | 7<br>note = Q at position 7 is chemically modified with a protecting group, such as a Fluorenylmethoxycarbonyl protecting group (Fmoc), tert-butyloxycarbonyl protecting group (Boc), or triphenylmethyl protecting group |
| SITE | 22<br>note = The C-terminal amino acid is amidated as a C-terminal primary amide |
| VARIANT | 2<br>note = Q at position 2 is chemically modified with a protecting group, such as a Fluorenylmethoxycarbonyl protecting group (Fmoc), tert-butyloxycarbonyl protecting group (Boc), or triphenylmethyl protecting group |
| VARIANT | 8<br>note = W at position 8 is chemically modified with a protecting group, such as a Fluorenylmethoxycarbonyl protecting group (Fmoc), tert-butyloxycarbonyl protecting group (Boc), or triphenylmethyl protecting group |
| VARIANT | 15<br>note = S at position 15 is chemically modified with a protecting group, such as a Fluorenylmethoxycarbonyl protecting group (Fmoc), tert-butyloxycarbonyl protecting group (Boc), or triphenylmethyl protecting group |
| VARIANT | 16<br>note = S at position 16 is chemically modified with a protecting group, such as a Fluorenylmethoxycarbonyl protecting group (Fmoc), tert-butyloxycarbonyl protecting group (Boc), or triphenylmethyl protecting group |
| VARIANT | 22<br>note = S at position 22 is chemically modified with a protecting group, such as a Fluorenylmethoxycarbonyl protecting group (Fmoc), tert-butyloxycarbonyl protecting group (Boc), or triphenylmethyl protecting group |
| SEQUENCE: 14 | |
| AQKAFVQWLI AGGPSSGAPP PS | 22 |
| | |
| SEQ ID NO: 15<br>FEATURE<br>source | moltype = AA  length = 15<br>Location/Qualifiers<br>1..15<br>mol_type = protein<br>organism = synthetic construct |
| SITE | 2<br>note = X at position 2 is Aib |
| SITE | 13<br>note = X at position 13 is Aib |
| VARIANT | 1<br>note = Y at position 1 is chemically modified with a protecting group, such as a Fluorenylmethoxycarbonyl protecting group (Fmoc), tert-butyloxycarbonyl protecting group (Boc), or triphenylmethyl protecting group |
| VARIANT | 3<br>note = E at position 3 is chemically modified with a protecting group, such as a Fluorenylmethoxycarbonyl protecting group (Fmoc), tert-butyloxycarbonyl protecting group (Boc), or triphenylmethyl protecting group |
| VARIANT | 5<br>note = T at position 5 is chemically modified with a protecting group, such as a Fluorenylmethoxycarbonyl protecting group (Fmoc), tert-butyloxycarbonyl protecting group (Boc), or triphenylmethyl protecting group |
| VARIANT | 7<br>note = T at position 7 is chemically modified with a protecting group, such as a Fluorenylmethoxycarbonyl protecting group (Fmoc), tert-butyloxycarbonyl protecting group (Boc), or triphenylmethyl protecting group |
| VARIANT | 8<br>note = S at position 8 is chemically modified with a protecting group, such as a Fluorenylmethoxycarbonyl protecting group (Fmoc), tert-butyloxycarbonyl protecting group (Boc), or triphenylmethyl protecting group |
| VARIANT | 9<br>note = D at position 9 is chemically modified with a |

|             |                                                                                                                                                                                                                       |
|-------------|-----------------------------------------------------------------------------------------------------------------------------------------------------------------------------------------------------------------------|
|             | protecting group, such as a Fluorenylmethoxycarbonyl protecting group (Fmoc), tert-butyloxycarbonyl protecting group (Boc), or triphenylmethyl protecting group                                                       |
| VARIANT     | 10                                                                                                                                                                                                                    |
|             | note = Y at position 10 is chemically modified with a protecting group, such as a Fluorenylmethoxycarbonyl protecting group (Fmoc), tert-butyloxycarbonyl protecting group (Boc), or triphenylmethyl protecting group |
| VARIANT     | 11                                                                                                                                                                                                                    |
|             | note = S at position 11 is chemically modified with a protecting group, such as a Fluorenylmethoxycarbonyl protecting group (Fmoc), tert-butyloxycarbonyl protecting group (Boc), or triphenylmethyl protecting group |
| VARIANT     | 15                                                                                                                                                                                                                    |
|             | note = D at position 15 is chemically modified with a protecting group, such as a Fluorenylmethoxycarbonyl protecting group (Fmoc), tert-butyloxycarbonyl protecting group (Boc), or triphenylmethyl protecting group |
| SITE        | 15                                                                                                                                                                                                                    |
|             | note = The C-terminal amino acid is amidated as a C-terminal primary amide                                                                                                                                            |
| SEQUENCE: 15 |                                                                                                                                                                                                                      |
| YXEGTFTSDY SIXLD | 15                                                                                                                                                                                                                |
|             |                                                                                                                                                                                                                       |
| SEQ ID NO: 16 | moltype = AA  length = 24                                                                                                                                                                                           |
| FEATURE     | Location/Qualifiers                                                                                                                                                                                                   |
| source      | 1..24                                                                                                                                                                                                                 |
|             | mol_type = protein                                                                                                                                                                                                    |
|             | organism = synthetic construct                                                                                                                                                                                        |
| SITE        | 5                                                                                                                                                                                                                     |
|             | note = K at position 5 is chemically modified through conjugation to the epsilon-amino group of the K side-chain with (2-[2-(2-Amino-ethoxy)-ethoxy]-acetyl)2-(gamma-Glu)-CO-(CH2)18-CO2H having carboxyl protecting groups |
| VARIANT     | 1                                                                                                                                                                                                                     |
|             | note = K at position 1 is chemically modified with a protecting group, such as a Fluorenylmethoxycarbonyl protecting group (Fmoc), tert-butyloxycarbonyl protecting group (Boc), or triphenylmethyl protecting group |
| VARIANT     | 4                                                                                                                                                                                                                     |
|             | note = Q at position 4 is chemically modified with a protecting group, such as a Fluorenylmethoxycarbonyl protecting group (Fmoc), tert-butyloxycarbonyl protecting group (Boc), or triphenylmethyl protecting group |
| SITE        | 24                                                                                                                                                                                                                    |
|             | note = The C-terminal amino acid is amidated as a C-terminal primary amide                                                                                                                                            |
| VARIANT     | 9                                                                                                                                                                                                                     |
|             | note = Q at position 9 is chemically modified with a protecting group, such as a Fluorenylmethoxycarbonyl protecting group (Fmoc), tert-butyloxycarbonyl protecting group (Boc), or triphenylmethyl protecting group |
| VARIANT     | 10                                                                                                                                                                                                                    |
|             | note = W at position 10 is chemically modified with a protecting group, such as a Fluorenylmethoxycarbonyl protecting group (Fmoc), tert-butyloxycarbonyl protecting group (Boc), or triphenylmethyl protecting group |
| VARIANT     | 17                                                                                                                                                                                                                    |
|             | note = S at position 17 is chemically modified with a protecting group, such as a Fluorenylmethoxycarbonyl protecting group (Fmoc), tert-butyloxycarbonyl protecting group (Boc), or triphenylmethyl protecting group |
| VARIANT     | 18                                                                                                                                                                                                                    |
|             | note = S at position 18 is chemically modified with a protecting group, such as a Fluorenylmethoxycarbonyl protecting group (Fmoc), tert-butyloxycarbonyl protecting group (Boc), or triphenylmethyl protecting group |

| | |
|---|---|
| VARIANT | 24 |
| | note = S at position 24 is chemically modified with a protecting group, such as a Fluorenylmethoxycarbonyl protecting group (Fmoc), tert-butyloxycarbonyl protecting group (Boc), or triphenylmethyl protecting group |
| SEQUENCE: 16 | |
| KIAQKAFVQW LIAGGPSSGA PPPS | 24 |
| | |
| SEQ ID NO: 17 | moltype = AA  length = 10 |
| FEATURE | Location/Qualifiers |
| source | 1..10 |
| | mol_type = protein |
| | organism = synthetic construct |
| SITE | 1 |
| | note = Fluorenylmethoxycarbonyl protecting group modified residue |
| SITE | 3 |
| | note = tert-butyl protecting group modified residue |
| SITE | 4 |
| | note = tert-butyl protecting group modified residue |
| SITE | 10 |
| | note = tert-butyl protecting group modified residue |
| SITE | 10 |
| | note = The C-terminal amino acid is amidated as a C-terminal primary amide |
| SEQUENCE: 17 | |
| GPSSGAPPPS | 10 |
| | |
| SEQ ID NO: 18 | moltype = AA  length = 10 |
| FEATURE | Location/Qualifiers |
| source | 1..10 |
| | mol_type = protein |
| | organism = synthetic construct |
| SITE | 1 |
| | note = Fluorenylmethoxycarbonyl protecting group modified residue |
| SITE | 3 |
| | note = tert-butyl protecting group modified residue |
| SITE | 4 |
| | note = tert-butyl protecting group modified residue |
| SITE | 10 |
| | note = tert-butyl protecting group modified residue |
| SEQUENCE: 18 | |
| GPSSGAPPPS | 10 |
| | |
| SEQ ID NO: 19 | moltype = AA  length = 5 |
| FEATURE | Location/Qualifiers |
| source | 1..5 |
| | mol_type = protein |
| | organism = synthetic construct |
| SITE | 1 |
| | note = Fluorenylmethoxycarbonyl protecting group modified residue |
| SITE | 3 |
| | note = tert-butyl protecting group modified residue |
| SITE | 4 |
| | note = tert-butyl protecting group modified residue |
| SEQUENCE: 19 | |
| GPSSG | 5 |

What is claimed is:

1. A process of preparing a compound of formula (I):

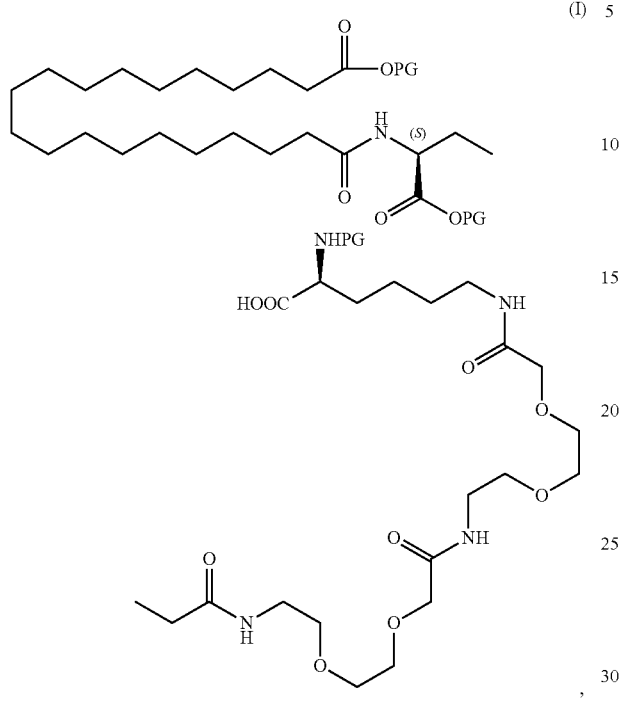

(I)

wherein PG is a protecting group, the process comprising:
(a) contacting a compound of formula (Ia) and diisopropylethylamine

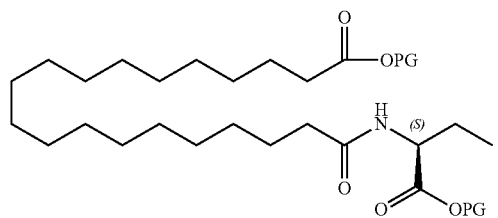

(Ia)

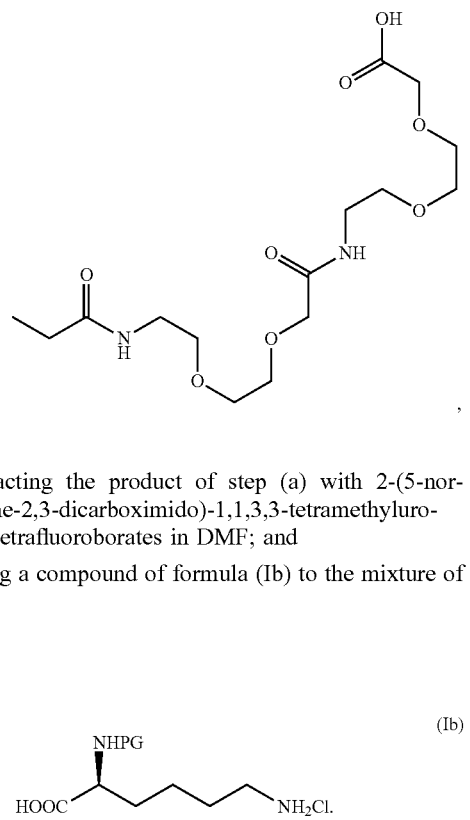

(b) contacting the product of step (a) with 2-(5-norbornene-2,3-dicarboximido)-1,1,3,3-tetramethyluronium tetrafluoroborates in DMF; and (c) adding a compound of formula (Ib) to the mixture of (b), (Ib)

2. The process of claim 1, wherein the protecting group is selected from the group consisting of Boc and Fmoc.

3. The process of claim 1 or 2, wherein the protecting group is Fmoc.

4. The process of any one of claims 1 to 3, wherein the process is conducted utilizing continuous flow.

5. The process of any one of claims 1-4, wherein the process is carried out in a flow reactor.

* * * * *